United States Patent
Kim

(10) Patent No.: US 11,195,594 B2
(45) Date of Patent: Dec. 7, 2021

(54) METHOD FOR SELECTING ANTICANCER AGENT BASED ON PROTEIN DAMAGE INFORMATION OF INDIVIDUAL TO PREVENT ANTICANCER AGENT SIDE EFFECTS

(71) Applicant: CIPHEROME, INC., Cupertino (CA)

(72) Inventor: Ju Han Kim, Seoul (KR)

(73) Assignee: Cipherome, Inc., San Jose, CA (US)

( * ) Notice: Subject to any disclaimer, the term of this patent is extended or adjusted under 35 U.S.C. 154(b) by 1133 days.

(21) Appl. No.: 15/550,004

(22) PCT Filed: Feb. 17, 2016

(86) PCT No.: PCT/KR2016/001630
§ 371 (c)(1),
(2) Date: Aug. 9, 2017

(87) PCT Pub. No.: WO2016/133373
PCT Pub. Date: Aug. 25, 2016

(65) Prior Publication Data
US 2018/0032664 A1 Feb. 1, 2018

(30) Foreign Application Priority Data

Feb. 17, 2015 (KR) .......................... 10-2015-0024443

(51) Int. Cl.
| | | |
|---|---|---|
| G16B 20/20 | (2019.01) | |
| G16B 20/00 | (2019.01) | |
| G16B 30/00 | (2019.01) | |
| G16B 50/00 | (2019.01) | |
| C12Q 1/6886 | (2018.01) | |
| G16B 30/10 | (2019.01) | |

(52) U.S. Cl.
CPC .......... *G16B 20/20* (2019.02); *C12Q 1/6886* (2013.01); *G16B 20/00* (2019.02); *G16B 30/00* (2019.02); *G16B 30/10* (2019.02); *G16B 50/00* (2019.02); *C12Q 2600/106* (2013.01); *C12Q 2600/156* (2013.01)

(58) Field of Classification Search
None
See application file for complete search history.

(56) References Cited

U.S. PATENT DOCUMENTS

| | | |
|---|---|---|
| 6,542,858 B1 | 4/2003 | Grass et al. |
| 2007/0299646 A1 | 12/2007 | Chemama et al. |
| 2011/0230360 A1 | 9/2011 | Dietrich et al. |
| 2012/0016594 A1 | 1/2012 | Christman et al. |
| 2012/0136583 A1 | 5/2012 | Lazar et al. |
| 2013/0184999 A1 | 7/2013 | Ding |

FOREIGN PATENT DOCUMENTS

| | | |
|---|---|---|
| CN | 102473202 A | 5/2012 |
| EP | 3037548 A1 | 6/2016 |
| JP | 2009-538631 A | 11/2009 |
| JP | 2012-533103 A | 12/2012 |
| KR | 10-2004-0103514 A | 12/2004 |
| KR | 10-2011-0119409 A | 11/2011 |
| KR | 10-2013-0093920 A | 8/2013 |
| WO | WO 2012/155148 A2 | 11/2012 |
| WO | WO 2012/174723 A1 | 12/2012 |

OTHER PUBLICATIONS

Baek, Su Yeon, "MedCassandra: Personalized Drug and ADR Ranking Forecast System Based on Personal Genome Variations," The Department of Biomedical Sciences, Seoul National University College of Medicine, Graduate School Master's degree thesis, Feb. 2013.
Baik et al., "MedCassandra: Personalized Drug and ADR Ranking Forecast System based on Personal Genome Variations," Graduate School Master's Degree Thesis, Seoul National University, Feb. 2013, pp. 1-29.
European Extended Search Report, European Application No. 14838351. 6, dated Feb. 24, 2017, 8 pages.
European Examination Report, European Application No. 14838351. 6, dated Feb. 12, 2018, 4 pages.
Japanese Office Action, Japanese Application No. 2016-536029, dated Jun. 27, 2017, 9 pages.
Kim, I. K., et al., "Clinical Pharmacogenomics of Drug Metabolizing Enzymes and its Clinical Application," 2006, Kor. J. Clin, Pharm., vol. 16, No. 2. (with English Abstract).
PCT Written Opinion, PCT Application No. PCT/KR2016/001630, dated May 12, 2016, 6 pages.
PCT International Search Report, PCT Application No. PCT/KR2014/ 007685, dated Nov. 21, 2014, 4 Pages.
PCT International Search Report and Written Opinion, PCT Application No. PCT/KR2016/001632, dated May 12, 2016, 15 pages.
Adzhubei, I. et al., "A method and server for predicting damaging missense mutations," Nature Methods, Apr. 1, 2010, pp. 248-249, vol. 7, No. 4.
China National Intellectual Property Administration, Notification of the First Office Action, CN Patent Application No. 201480046187. 7, dated Mar. 5, 2019, 76 pages.
European Patent Office, Extended European Search Report and Opinion, European Patent Application 19153339.7, dated Apr. 4, 2019, 9 pages.
European Patent Office, Extended European Search Report and Opinion, European Patent Application 16752703.5, dated Jan. 17, 2019, 7 pages.

(Continued)

*Primary Examiner* — G Steven Vanni
(74) *Attorney, Agent, or Firm* — Fenwick & West LLP

(57) ABSTRACT

The present invention relates to a method and a system for selecting an anticancer agent based on protein damage information of an individual by using individual genome sequencing. The method and the system, according to the present invention, are highly reliable and widely applicable techniques capable of predicting side effects or risks of specific drugs, in other words, anticancer agents, for each individual by performing sequence analysis of an exon part of a gene that codes various proteins involved in pharmacokinetics or pharmacodynamics of anticancer agents.

18 Claims, 4 Drawing Sheets

(56) References Cited

OTHER PUBLICATIONS

Sacerdote, C. et al., "Polymorphisms in the *XRCC1* gene modify survival of bladder cancer patients treated with chemotherapy," International Journal of Cancer, Mar. 30, 2013, pp. 2004-2009, vol. 133, No. 8.
PCT International Search Report, PCT/KR2016/001630, dated May 12, 2016, 5 Pages.
Baek, S. Y., "MedCassandra: Personalized Drug and ADR Ranking Forecast System based on Personal Genome Variations," Master of Medical Science, Department of Biomedical Sciences, Feb. 2013.
NG, P.C. et al., "Predicting Deleterious Amino Acid Substitutions," Genome Research, 2001, pp. 863-874, vol. 11, No. 5.

[FIG.1]
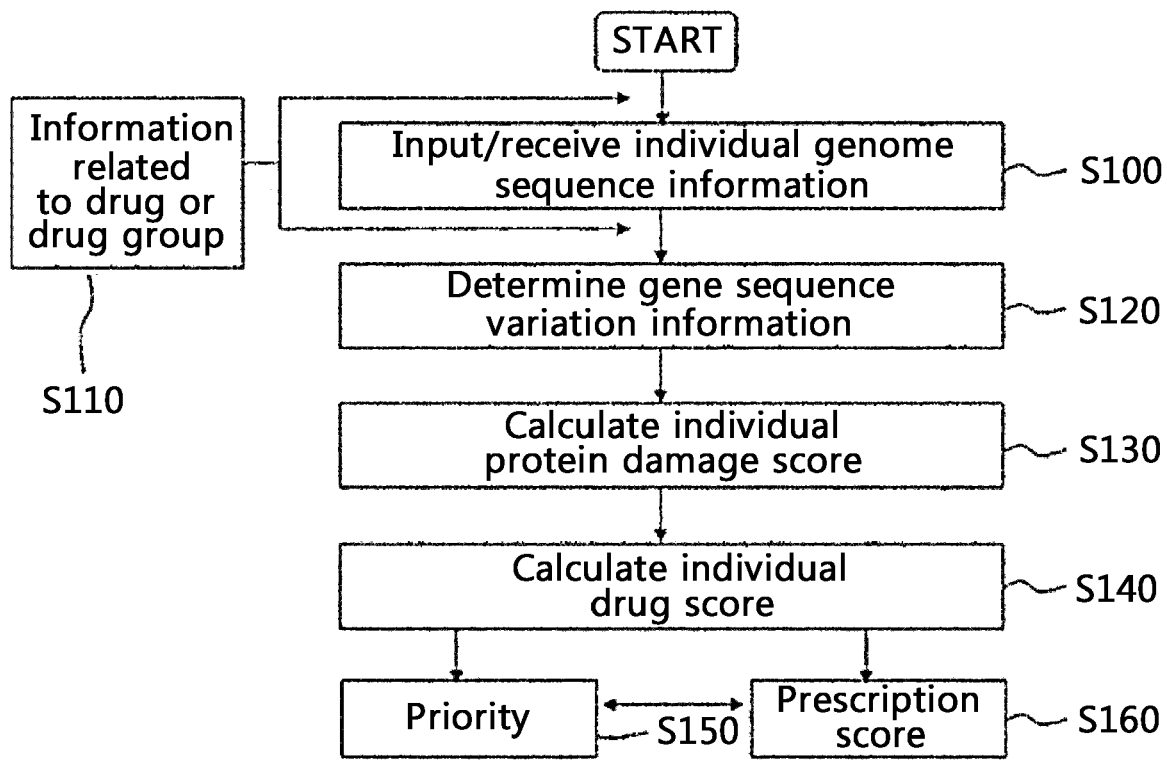

[FIG. 2]
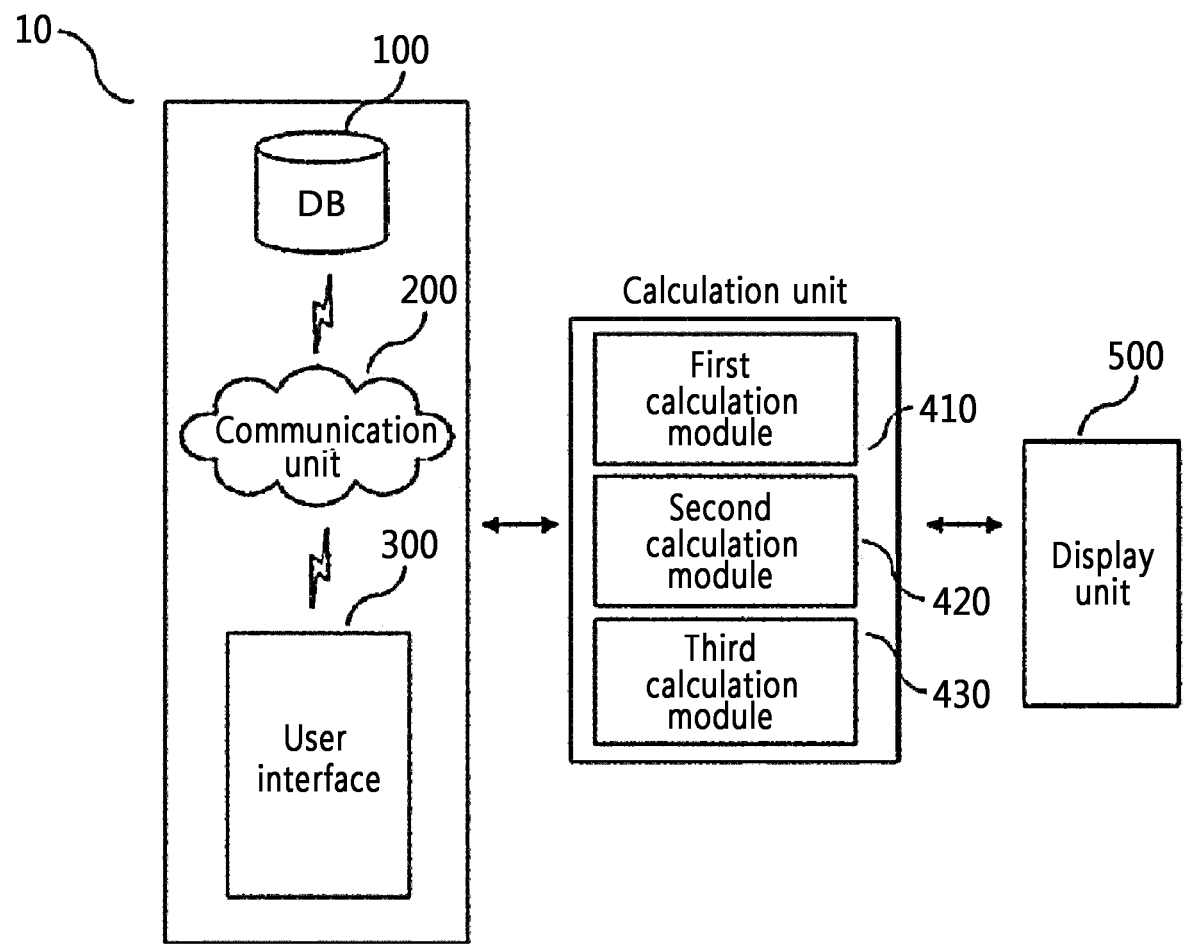

METHOD FOR SELECTING ANTICANCER AGENT BASED ON PROTEIN DAMAGE INFORMATION OF INDIVIDUAL TO PREVENT ANTICANCER AGENT SIDE EFFECTS

CROSS-REFERENCE TO RELATED APPLICATIONS

This application is the National Stage of International Application No. PCT/KR2016/001630, filed Feb. 17, 2016, which claims the benefit of and priority to Korean Application No. 10-2015-0024443, filed Feb. 17, 2015, all of which are incorporated by reference herein in their entirety.

TECHNICAL FIELD

The present disclosure relates to a method for selecting an anticancer agent based on protein damage information of an individual for preventing side effects of an anticancer agent, specifically to a method for selecting an anticancer agent using individual genome sequencing.

BACKGROUND ART

With the advancement of biotechnology technologies, it is now possible to analyze the whole genome sequence of a human and to predict a disease of each individual and provide personalized prevention and treatment of the disease.

Recently, as a result of comparison of individual genome sequences, it was found that different bases may be present at the same position in chromosomes. Accordingly, such difference in sequences has been used to predict individuals' difference in drug response. For example, drug metabolism may be slow or fast depending on a specific genome sequence information of an individual, and, thus, therapeutic effects or side effects of a drug may be different for each individual.

Accordingly, there has been an increase in a demand for personalized drug selection which is capable of selecting a drug and a dose suitable for a patient by using the difference of individual genome sequences. Also, pharmacogenetics or pharmacogenomics, which uses genomic information, e.g., single nucleotide polymorphism (SNP), as a marker and correlation between the marker and drug response/drug side effect, has emerged.

In pharmacogenetics, differences in metabolism of drugs or chemicals and response thereto in a general population or between individuals are predicted by genetic analysis. Some individuals may show unexpected drug responses. Such drug side effects may be due to severity of a disease under treatment, drug interaction, ages, nutritive conditions, liver and kidney functions of patients, and environmental factors such as weather or diet. However, they may be also caused by drug metabolism-related genetic differences, for example, polymorphism of drug-metabolizing enzymes. Therefore, study is being conducted in this regard.

Busulfan, which is an anticancer agent and myelosuppressive, is primarily used prior to bone marrow transplantation for ablation of bone marrow. Busulfan has a very narrow therapeutic window between lethal myelotoxicity and endurable systemic toxicity. Busulfan has the problem that severe drug toxicity occurs when the drug concentration is higher than the therapeutic range and the risk of graft failure or relapse increases when the drug concentration is lower than the therapeutic range. The toxicity of busulfan includes interstitial pulmonary fibrosis commonly called "busulfan lung", hyperpigmentation, epilepsy, hepatic veno-occlusive disease (VOD), emesis, thrombocytopenia, etc. The likelihood of these problems is high because the pharmacokinetics of busulfan varies greatly between individuals.

In order to reduce the preconditioning-associated toxicity, a method of administering an adequate dose of busulfan which is determined through a pharmacokinetic model after administration of a test dose or an initial dose was disclosed (Kletzel M, 2006, Bartelink I H, 2008). However, it is not adopted globally because the pharmacokinetic modeling requires blood sampling of at least 4-5 times a day as well as measurement and pharmacokinetic analysis on the test day and the expensive liquid chromatography/tandem mass spectrometry system is necessary. In addition, because the drug has to be administered, it is difficult to predict an adequate dose in advance and prevent complications.

Pharmacogenomics may be used to predict the side effect of a drug prior to its administration. For busulfan too, it is known that its blood level and side effects are associated with its pharmacogenomics. In a pharmacogenomics study of busulfan on children, it was reported that the GSTM1 gene affects the pharmacokinetics of busulfan (Ansari M. et al, 2010). Also, it was reported that the blood level of busulfan can be varied by the polymorphism of GSTA1, which is an important drug-metabolizing enzyme (Kusama M. et al, 2006).

Thiopurine-based drugs with similar metabolic pathways are usefully used for various purposes, including treatment of hematoma, treatment of rheumatoid diseases, immunosuppression in organ transplantation, etc. As one of the thiopurine-based drugs, azathioprine is used as an immunosuppressive medication in treatment of ulcerative colitis, which is an inflammatory bowel disease, and Crohn's disease. During the treatment, some patients suffer from bone marrow suppression and leukopenia. It is known that this is closely related with the genetic polymorphism of the TPMT gene which encodes thiopurine S-methyltransferase. Thiopurine S-methyltransferase is an enzyme which metabolizes thiopurine-based drugs. Some known genotypes for TPMT disturb the metabolism of thiopurine-based drugs by inhibiting or suppressing the function of TPMT. It is known that serious side effects such as bone marrow suppression may occur in patients who have such genotypes that suppress the function of TPMT.

As another thiopurine-based drug, mercaptopurine is used together with other drugs for maintenance therapy in the treatment of acute lymphocytic leukemia. Like azathioprine, mercaptopurine may also cause severe life-threatening side effects such as leukopenia or agranulocytosis. Because mercaptopurine is a thiopurine-based drug too, the relationship between the variation of the TPMT gene and the side effects of mercaptopurine is known.

Although the variation of the TPMT gene is not observed frequently in Asians, they show higher prevalence of leukopenia caused by thiopurine-based drugs. According to a study (Yang, S. K., Hong, M., Baek, J., Choi, H., Zhao, W., Jung, Y., . . . & Park, S. K. (2014). A common missense variant in NUDT15 confers susceptibility to thiopurine-induced leukopenia. *Nature Genetics*, 46(9), 1017-1020.), Crohn's disease patients treated with thiopurine-based drugs showed a high correlation between the variation of the NUDT15 gene and the leukopenia occurring during thiopurine therapies.

At present, it is known that the genetic variation of tens to hundreds of drug metabolism-related genes affects the function of corresponding proteins in the metabolism of drugs in the body, thereby promoting or suppressing the drug metabolism. Although it is also necessary to elucidate new genetic variations, it is limited to understand all the various drug metabolism-related genes through analysis of a small number of genes. Therefore, introduction of a methodology beyond the method based on a result of population observational studies using a small number of genes or markers such as single nucleotide polymorphism is necessary. It is strongly needed to introduce a method for providing information for selecting a personalized anticancer agent, which is more useful and reliable, by directly using individual genome sequence variation information and conducting theoretical deduction on protein damage caused thereby and biological effect thereof.

DETAILED DESCRIPTION OF INVENTION

Technical Problem

The present disclosure, which is conceived in view of the foregoing, provides a method for providing information for selecting an anticancer agent by analyzing individual genome sequence variation information, calculating an individual protein damage score from gene sequence variation information involved in the pharmacodynamics or pharmacokinetics of an anticancer agent, a myelosuppressive or an immunosuppressant having a similar metabolic pathway and calculating an individual drug score by associating the score with a drug-protein relation so as to predict the likelihood of the side effect of the anticancer agent.

Technical Solution

In an aspect, the present disclosure provides a method for providing information for selecting an anticancer agent using individual genome sequence variation, which includes: a step of determining one or more gene sequence variation information involved in the pharmacodynamics or pharmacokinetics of an anticancer agent from individual genome sequence information; a step of calculating an individual protein damage score using the gene sequence variation information; and a step of calculating an individual drug score by associating the individual protein damage score with a drug-protein relation.

In another aspect, the present disclosure provides a system for selecting an anticancer agent using individual genome sequence variation, which includes: a database from which information relevant to a gene or protein related to an anticancer agent applicable to an individual can be searched or extracted; a communication unit which is accessible to the database; a first calculation module which is configured to calculate one or more gene sequence variation information involved in the pharmacodynamics or pharmacokinetics of the anticancer agent based on the information; a second calculation module which is configured to calculate an individual protein damage score using the gene sequence variation information; a third calculation module which is configured to calculate an individual drug score by associating the individual protein damage score with a drug-protein relation; and a display unit which is configured to display the values calculated by the calculation modules.

In another aspect, the present disclosure provides a computer-readable medium including an execution module for executing a processor which performs an operation including: a step of acquiring one or more gene sequence variation information involved in the pharmacodynamics or pharmacokinetics of an anticancer agent from individual genome sequence information; a step of calculating an individual protein damage score using the gene sequence variation information; and a step of calculating an individual drug score by associating the individual protein damage score with a drug-protein relation.

Advantageous Effects

A method and a system for selecting a personalized anticancer agent based on individual genome sequence variation information of the present disclosure can predict the response of an individual to a specific drug, i.e., an anticancer agent, by analyzing the sequence of the exon region of a gene encoding various proteins involved in the pharmacodynamics or pharmacokinetics of the anticancer agent.

The existing method of controlling the administration dose of busulfan based on pharmacokinetic modeling is not adopted widely because blood sampling is necessary several times a day and expensive equipment is necessary for instant analysis of the blood sample. In contrast, as it has become easy to use genotyping techniques (PCR, SNP chip, capillary sequencing, NGS, etc.) for clinical applications with the advance in experimental methods, it is expected that the present disclosure based on pharmacogenomics can be widely used in clinical settings. In particular, as the price of next-generation sequencing (NGS) falls rapidly, genomic approach has become possible at the cost of tens to hundreds of thousands of won per patient.

Further, the existing pharmacogenomic study needs to be conducted on the basis of drug-gene pairs. However, it is practically impossible to study all of the numerous drug-gene pairs because the number of pairs increases in proportion to the multiple of the number of drugs and the number of gene markers. Thus, sufficient supporting data have not yet been generated. In addition, large statistical errors may occur depending on the population groups selected. In contrast, according to the method of the present disclosure, results of study and analysis at a molecular level are directly applied to personalized drug treatment, and, thus, grounds can be established for almost all drug-gene pairs and the method can be applied without being significantly affected by the difference between population groups.

In particular, the method and the system of the present disclosure may be usefully used to determine whether an anticancer agent, e.g., busulfan, can be used for an individual and how it will be used by predicting the side effect or risk of the drug in advance. This may lead to improved survival rate of patients with childhood cancer through administration of busulfan at optimum doses. In addition, a new therapeutic regimen may be introduced for patient groups for whom hematopoietic stem cell transplantation was not easy due to difficulty in preconditioning by improving the safety of busulfan preconditioning.

The present disclosure may also be usefully used to determine whether mercaptopurine, which is another anticancer agent, can be used for an individual and how it will be used by predicting the side effect or risk of the drug in advance. This may lead to improved survival rate and decreased cost of treatment by preventing prolonged hospitalization or aggravated physical conditions of patients caused by side effects such as leukopenia, etc. during the treatment.

Further, if new information about an anticancer agent-protein relation is found or provided, it can be easily added and applied to the method of the present disclosure. Thus, it is possible to provide an improved personalized drug treatment method according to further accumulation of information.

BRIEF DESCRIPTION OF DRAWINGS

FIG. 1 is a flowchart illustrating each step of a method for providing information for selecting an anticancer agent using individual genome sequence variation according to an exemplary embodiment of the present disclosure.

FIG. 2 schematically illustrates the configuration of a system for selecting an anticancer agent using individual genome sequence variation according to an exemplary embodiment of the present disclosure (DB: database).

MODE FOR CARRYING OUT INVENTION

Figure 3A:
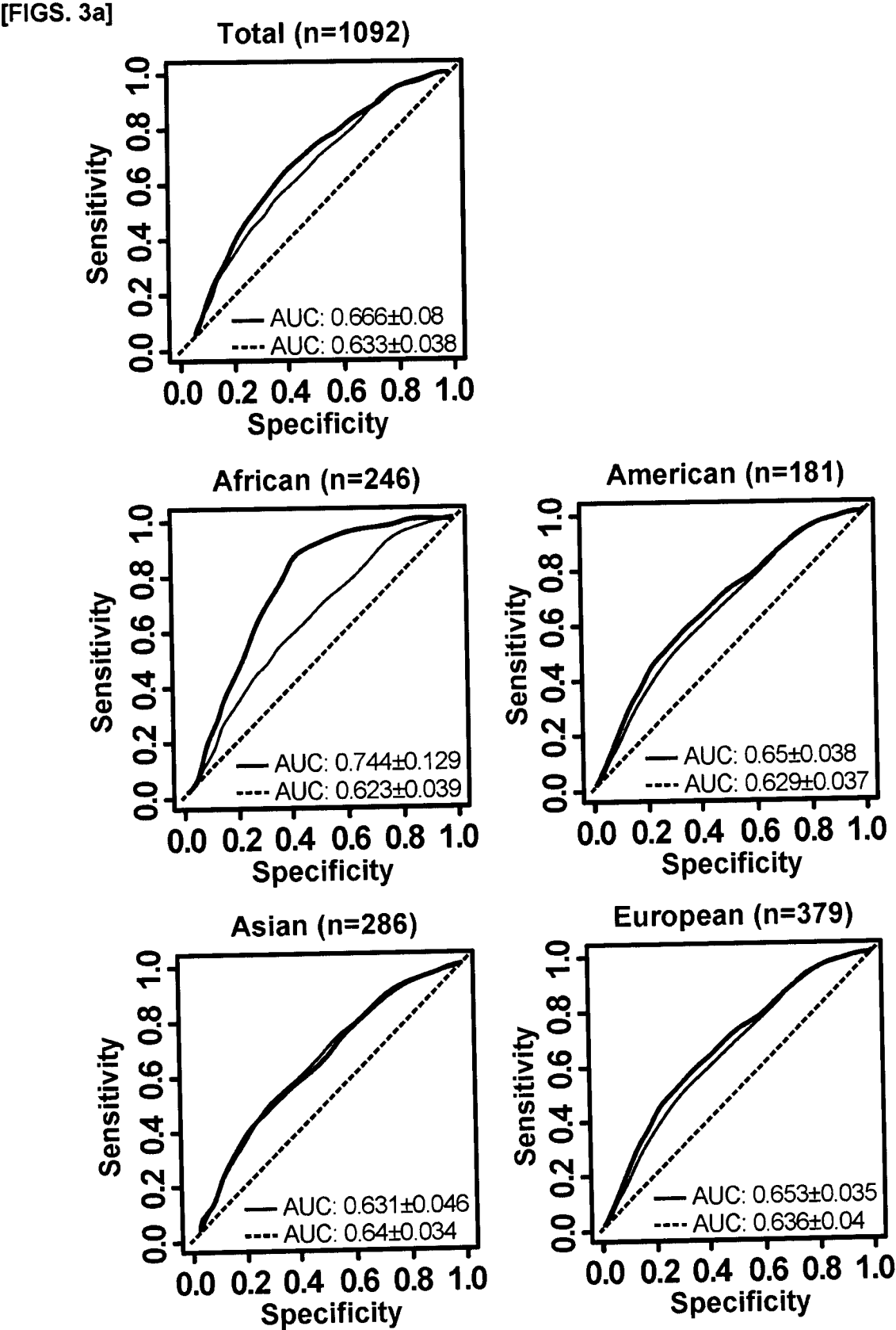
FIGS. 3A-3B show ROC (receiver operating characteristic) curves for verifying a method for selecting an anticancer agent using genome sequence variation according to an exemplary embodiment of the present disclosure.

The present disclosure is based on the finding that it is possible to select a drug with high safety and its dose/usage personalized for an individual in a drug therapy by analyzing individual genome sequence variation information.

In an aspect, the present disclosure relates to a method for providing information for selecting an anticancer agent using individual genome sequence variation, which includes: a step of determining one or more gene sequence variation information involved in the pharmacodynamics or pharmacokinetics of an anticancer agent from individual genome sequence information; a step of calculating an individual protein damage score using the gene sequence variation information; and a step of calculating an individual drug score by associating the individual protein damage score with a drug-protein relation.

In the present disclosure, the anticancer agent includes the drugs described in Table 1 below and any substance exhibiting the same or similar pharmacological activity, including derivatives thereof, pharmaceutically acceptable salts thereof, etc. For example, it may be a thiopurine-based drug including thioguanine, mercaptopurine and azathioprine, a deoxynucleoside analog including cladribine, fludarabine, clofarabine and nelarabine, an alkylating agent including treosulfan, mannosulfan and busulfan, an antimetabolite, an antimicrotubule agent, a topoisomerase inhibitor, a cytotoxic antibody, etc., specifically busulfan or mercaptopurine, although not being limited thereto.

In the present disclosure, the information of the genes involved in the pharmacodynamics or pharmacokinetics of the anticancer agent may be obtained from such databases as DrugBank, KEGG Drug, PharmGKB, etc. Specifically, the gene includes ABCC1, ABCG2, APEX1, CBR3, ATP7A, CBR3, CTH, CUL9, CYP1A1, CYP2C9, CYP2D6, CYP4B1, DPEP1, DPEP2, DPYD, DRD3, EPHX1, FMO2, FMO3, GGT1, GGT5, GGT6, GNB3, GSTA2, GSTM1, MGMT, MLH1, MSH2, NAT1, OPRM1, PDE5A, PTGS1, SERPINA6, SLC15A2, SLC22A1, SLC22A2, SLC22A8, SLC22A16, SLC22A2, SLC28A2, SLC28A3, SPG7, TP53, ABCB1, ABCC2, AOX1, CHRM2, CYP1B1, CYP3A4, CYP3A5, CYP4F2, DBH, ERCC2, GGH, GGT7, GMPS, MTHFR, NUDT15, PDE3A, PDE4C, SLC22A5, SLCO1B1, TLR3, UGT1A1, XDH, etc., although not being limited thereto.

In the present disclosure, genes/proteins are named according to the HGNC (HUGO Gene Nomenclature Committee) nomenclature (Gray K A, Daugherty L C, Gordon S M, Seal R L, Wright M W, Bruford E A. genenames.org: the HGNC resources in 2013. *Nucleic Acids Res.* 2013 January; 41 (Database issue): D545-52. doi: 10.1093/nar/gks1066. Epub 2012 Nov. 17 PMID: 23161694).

In the present disclosure, the gene sequence variation used as information refers to individual gene sequence variation or polymorphism. In the present disclosure, the gene sequence variation or polymorphism occurs in a region, particularly an exon region, of a gene encoding proteins involved in the pharmacodynamics or pharmacokinetics of an anticancer agent, although not being limited thereto.

The term "sequence variation information" used in the present disclosure means information about substitution, addition or deletion of a base constituting an exon of a gene. Such substitution, addition or deletion of the base may result from various causes, for example, structural differences including mutation, breakage, deletion, duplication, inversion and/or translocation of a chromosome.

In another aspect, a polymorphism of a sequence refers to differences in a sequence between individuals present in a genome. Single nucleotide polymorphism (SNP) is the most frequent form of the polymorphism of a sequence. It refers to variation in one base of a sequence consisting of A, T, C and G between individuals. The sequence polymorphism

TABLE 1

| | | | | | |
|---|---|---|---|---|---|
| Temozolomide | Gefitinib | Amsacrine | Ethinyl Estradiol | Fluorouracil | Trastuzumab |
| Trastuzumab (genetical recombination) | Megestrol | Celecoxib | Flutamide | Ifosfamide | Dasatinib |
| Procarbazine | Fulvestrant | Temsirolimus | Pemetrexed | Histamine | Tamoxifen |
| Ciclosporin | Letrozole | Medroxyrogesterone | Capecitabine | Daunorubicin | Sorafenib |
| Exemestane | Dactinomycin | Nilutamide | Oxaliplatin | Vinorelbine | Imatinib |
| Thioguanine | Topotecan | Aminoglutethimide | Erlotinib | Vindesine | Cyclosporine |
| Mitomycin | Hydroxyurea | Mercaptopurine | Gemcitabine | Etoposide | Vincristine |
| Ixabepilone | Aminolevulinic acid | Mitoxantrone | Teniposide | Diethylstilbestrol | Vinblastine |
| Busulfan | Azathioprine | Idarubicin | Cyclophosphamide | Epirubicin | Paclitaxel |
| Lomustine | Bicalutamide | Trabectedin | Cisplatin | Thalidomide | Bortezomib |
| Streptozocin | Toremifene | Dacarbazine | Cytidine | Cladribine | Tretinoin |
| Thiotepa | Anastrozole | Bexarotene | Arsenic trioxide | Irinotecan | Methotrexate |
| Gemtuzumab ozogamicin (genetical recombination) | Clofarabine | Estramustine | Nilotinib | Sunitinib | Nelarabine |
| Everolimus | Fludarabine | Lapatinib | Sirolimus | Docetaxel | Treosulfan |
| Afatinib | Cabazitaxel | Tacrolimus | Leflunomide | Ethanol | Mannosulfan | including the SNP can occur as SNV (single nucleotide variation), STRP (short tandem repeat polymorphism) or a polyalleic variation including VNTR (various number of tandem repeat) and CNV (copy number variation).

In the method of the present disclosure, the sequence variation or polymorphism information found in an individual genome is collected in association with a protein involved in the pharmacodynamics or pharmacokinetics of an anticancer agent. That is to say, the sequence variation information used in the method of the present disclosure is variation information found particularly in an exon region of one or more gene involved in the pharmacodynamics or pharmacokinetics of an anticancer agent, for example, a gene encoding a target protein relevant to a drug, an enzyme protein involved in drug metabolism, a transporter protein or a carrier protein, among the obtained individual genome sequence information, although not being limited thereto.

The individual genome sequence information used in the present disclosure may be determined using a well-known sequencing method. Further, commercially available services provided by Complete Genomics, BGI (Beijing Genome Institute), Knome, Macrogen, DNALink, etc. may be used, although not being limited thereto.

In the present disclosure, the gene sequence variation information present in an individual genome sequence may be extracted by using various methods and may be acquired through comparative analysis of sequences using a program, for example, ANNOVAR (Wang et al., *Nucleic Acids Research,* 2010; 38(16): e164), SVA (Sequence Variant Analyzer) (Ge et al., *Bioinformatics.* 2011; 27(14): 1998-2000), BreakDancer (Chen et al., *Nat Methods.* 2009 Sep.; 6(9):677-81), and the like, which compare the sequence with a reference group, for example, the genome sequence of HG19.

The gene sequence variation information may be received/acquired through a computer system. In this aspect, the method of the present disclosure may further include a step of receiving the gene sequence variation information through a computer system. The computer system used in the present disclosure may include or be accessible to one or more database containing information about the gene involved in the pharmacodynamics or pharmacokinetics of the anticancer agent, for example, a gene encoding a target protein relevant to a drug, an enzyme protein involved in drug metabolism, a transporter protein, a carrier protein, etc. These databases may include a public or non-public database or a knowledge base, which provides information about gene/protein/drug-protein interactions, etc., including, for example, DrugBank, KEGG Drug and PharmGKB, although not being limited thereto.

In the present disclosure, the anticancer agent may be information input by a user, information input from a prescription or information input from a database including information about anticancer agents. The prescription may include an electronic prescription, although not being limited thereto.

The term "pharmacokinetics (PK) or pharmacokinetic parameters" used in the present disclosure refers to characteristics of a drug involved in absorption, migration, distribution, conversion and excretion of the drug in the body for a predetermined time period, and includes the volume of distribution ($V_d$), clearance rate (CL), bioavailability (F) and absorption rate coefficient ($k_a$) of a drug or the maximum plasma concentration ($C_{max}$), time point of maximum plasma concentration ($T_{max}$), area under the curve (AUC) regarding the change in the blood level of a drug for a certain time period, etc.

The term "pharmacodynamics or pharmacodynamic parameters" used in the present disclosure refers to characteristics involved in the physiological and biochemical actions of a drug with respect to the body and mechanisms thereof, i.e., responses or effects in the body caused by the drug.

The term "gene sequence variation score" used in the present disclosure refers to a numerical score of a degree of the individual genome sequence variation that causes an amino acid sequence variation (substitution, addition or deletion) of a protein encoded by a gene or a transcription control variation and thus causes a significant change or damage to a structure and/or function of the protein when the genome sequence variation is found in an exon region of the gene encoding the protein. The gene sequence variation score can be calculated considering a degree of evolutionary conservation of amino acid in a genome sequence, a degree of an effect of a physical characteristic of modified amino acid on a structure or function of the corresponding protein.

The gene sequence variation score used for calculating the individual protein damage score and the individual drug score according to the present disclosure can be calculated by using a method known in the art. For example, the gene sequence variation score can be calculated from the gene sequence variation information using an algorithm such as SIFT (Sorting Intolerant From Tolerant, Pauline C et al., *Genome Res.* 2001 May; 11(5): 863-874; Pauline C et al., *Genome Res.* 2002 March; 12(3): 436-446; Jing Hul et al., Genome Biol. 2012; 13(2): R9), PolyPhen, PolyPhen-2 (Polymorphism Phenotyping, Ramensky V et al., *Nucleic Acids Res.* 2002 Sep. 1; 30(17): 3894-3900; Adzhubei IA et al., *Nat Methods* 7(4): 248-249 (2010)), MAPP (Eric A. et al., Multivariate Analysis of Protein Polymorphism, *Genome Research* 2005; 15: 978-986), Logre (Log R Pfam E-value, Clifford R. J et al., *Bioinformatics* 2004; 20: 1006-1014), Mutation Assessor (Reva B et al., *Genome Biol.* 2007; 8: R232, Condel (Gonzalez-Perez A et al., *The American Journal of Human Genetics* 2011; 88: 440-449, GERP (Cooper et al., Genomic Evolutionary Rate Profiling, *Genome Res.* 2005; 15: 901-913, CADD (Combined Annotation-Dependent Depletion, MutationTaster, MutationTaster2 (Schwarz et al., MutationTaster2: mutation prediction for the deep-sequencing age. *Nature Methods* 2014; 11: 361-362, PROVEAN (Choi et al., *PLoS One.* 2012; 7(10): e46688), PMut (Ferrer-Costa et al., *Proteins* 2004; 57(4): 811-819, CEO (Combinatorial Entropy Optimization, Reva et al., *Genome Biol* 2007; 8(11): R232), SNPeffect (Reumers et al., *Bioinformatics.* 2006; 22(17): 2183-2185, fathmm (Shihab et al., Functional Analysis through Hidden Markov Models, *Hum Mutat* 2013; 34: 57-65, etc., although not being limited thereto.

The above-described algorithms are configured to identify how much effect each gene sequence variation has on a protein function, how much the effect damage the protein or whether or not there are any other effects. These algorithms are basically configured to consider an amino acid sequence of a protein encoded by a corresponding gene and its relevant change caused by an individual gene sequence variation and thereby to determine an effect on a structure and/or function of the corresponding protein.

In an exemplary embodiment of the present disclosure, the SIFT (Sorting Intolerant From Tolerant) algorithm is used to calculate an individual gene sequence variation score. In the case of the SIFT algorithm, for example, gene sequence variation information is input in the form of a VCF (Variant Call Format) file and a degree of damage caused by each gene sequence variation to the corresponding gene is scored. In the case of the SIFT algorithm, as a calculated score is closer to 0, it is considered that a protein encoded by a corresponding gene is severely damaged and thus its function is damaged, and as the calculated score is closer to 1, it is considered that the protein encoded by the corresponding gene maintains its normal function.

In the case of another algorithm PolyPhen-2, the higher a calculated score is, it is considered that the function of a protein encoded by a corresponding gene is more damaged.

Recently, a study (González-Pérez, A. & López-Bigas, N. Improving the assessment of the outcome of nonsynonymous SNVs with a consensus deleteriousness score, Condel. *The American Journal of Human Genetics*, 2011; 88(4): 440-449.) suggesting the Condel algorithm by comparing and combining SIFT, Polyphen2, MAPP, Logre and Mutation Assessor was reported. In this study, the above-described five algorithms are compared by using HumVar and HumDiv (Adzhubei, IA et al., A method and server for predicting damaging missense mutations. *Nature methods*, 2010; 7(4): 248-249) as a set of known data relating to gene sequence variations damaging a protein and gene sequence variations with less effects. As a result, 97.9% of the gene sequence variations damaging a protein and 97.3% of the gene sequence variations with less effects of HumVar were identically detected by at least three of the above-described five algorithms, and 99.7% of the gene sequence variations damaging a protein and the 98.8% of gene sequence variations with less effects of HumDiv were identically detected by at least three of the above-described five algorithms. Further, as a result of drawing an ROC (receiver operating characteristic) curve showing accuracy of the calculation results of the five algorithms and a combination of the algorithms utilizing HumDiv and HumVar, it was confirmed that an AUC (area under the receiver operating characteristic curve) consistency is considerably high (69% to 88.2%). That is to say, the above-described algorithms are different in calculation methods but the calculated gene sequence variation scores are significantly correlated to each other. Therefore, it is included in the scope of the present disclosure regardless of the particular algorithms calculating gene sequence variation scores to apply a gene sequence variation score calculated by applying the above-described algorithms or a method employing the algorithms to the steps of calculating an individual protein damage score and an individual drug score according to the present disclosure.

When a gene sequence variation occurs in the exon region of a gene encoding a protein, the gene sequence variation may directly affect the structure and/or function of the protein. Therefore, the gene sequence variation information may be associated with the degree of damage to a protein function. In this aspect, the method of the present disclosure calculates an individual protein damage score on the basis of the above-described gene sequence variation score in the following step.

The term "protein damage score" used in the present disclosure refers to a score calculated by summarizing gene sequence variation scores when two or more significant sequence variations are found in a gene region encoding a single protein so that the single protein has two or more gene sequence variation scores. If there is a single significant sequence variation in the gene region encoding the protein, a gene sequence variation score is identical to a protein damage score. Herein, if there are two or more gene sequence variations encoding a protein, a protein damage score is calculated as a mean of gene sequence variation scores calculated for the respective variations. Such a mean can be calculated by, for example, but not limited to, measuring a geometric mean, an arithmetic mean, a harmonic mean, an arithmetic geometric mean, an arithmetic harmonic mean, a geometric harmonic mean, a Pythagorean mean, an interquartile mean, a quadratic mean, a truncated mean, a winsorized mean, a weighted mean, a weighted geometric mean, a weighted arithmetic mean, a weighted harmonic mean, a mean of a function, a generalized mean, a generalized f-mean, a percentile, a maximum value, a minimum value, a mode, a median, a mid-range, a central tendency, a simple multiplication or a weighted multiplication, or by a functional operation of the calculated values, although not being limited thereto.

In an exemplary embodiment of the present disclosure, the protein damage score is calculated by Equation 1. The following Equation 1 can be modified in various ways, and, thus, the present disclosure is not limited thereto.

$$S_g(v_1,\ldots,v_n) = \left(\frac{1}{n}\sum_{i=1}^{n} v_i^p\right)^{\frac{1}{p}} \quad \text{[Equation 1]}$$

In Equation 1, $S_g$ is a protein damage score of a protein encoded by a gene g, n is the number of target sequence variations to be analyzed among sequence variations of the gene g, $v_i$ is a gene sequence variation score of an i-th gene sequence variation and p is a real number other than 0. In Equation 1, when a value of the p is 1, the protein damage score is an arithmetic mean, if the value of the p is −1, the protein damage score is a harmonic mean, and if the value of the p is close to the limit 0, the protein damage score is a geometric mean.

In another exemplary embodiment of the present disclosure, the protein damage score is calculated by Equation 2. The following Equation 2 can be modified in various ways, and, thus, the present disclosure is not limited thereto.

$$S_g(v_1,\ldots,v_n) = \left(\prod_{i=1}^{n} v_i^{\omega_i}\right)^{1/\sum_{i=1}^{n} \omega_i} \quad \text{[Equation 2]}$$

In Equation 2, $S_g$ is a protein damage score of a protein encoded by a gene g, n is the number of target sequence variations to be analyzed among sequence variations of the gene g, $v_i$ is a gene sequence variation score of an i-th gene sequence variation and $w_i$ is a weighting assigned to the $v_i$. If all the weightings $w_i$ have the same value, the protein damage score $S_g$ is a geometric mean of the gene sequence variation scores $v_i$. The weighting may be assigned considering a class of the corresponding protein, pharmacodynamic or pharmacokinetic classification of the corresponding protein, pharmacokinetic parameters of the enzyme protein of a corresponding drug, a population group, or a race distribution.

The "pharmacokinetic parameters of a drug-metabolizing enzyme" used in the present disclosure include $V_{max}$, $K_m$, $K_{cat}/K_m$, etc. $V_{max}$ is the maximum enzyme reaction rate when a substrate concentration is very high, and $K_m$ is the substrate concentration that causes the reaction to reach ½ $V_{max}$. $K_m$ may be regarded as the affinity between the corresponding enzyme and the corresponding substrate. As the $K_m$ is decreased, the bonding force between the corresponding enzyme and the corresponding substrate is increased. $K_{cat}$, also called the turnover number of an enzyme, refers to the number of substrate molecules metabolized in 1 second in each enzyme active site when the enzyme is activated at a maximum rate, and means how fast the enzyme reaction actually occurs.

According to the method of the present disclosure, an individual drug score is calculated in the following step by associating the above-described protein damage score with a drug-protein relation.

The term "drug score" used in the present disclosure refers to a value calculated with respect to a predetermined drug, e.g., an anticancer agent, by finding out a target protein involved in the pharmacodynamics or pharmacokinetics of the drug, an enzyme protein involved in drug metabolism, a transporter protein or a carrier protein, calculating protein damage scores of the proteins and summarizing the scores.

In the present disclosure, if two or more proteins involved in the pharmacodynamics or pharmacokinetics of an anticancer agent are damaged, the drug score is calculated as a mean of the protein damage scores. Such a mean can be calculated by, for example, measuring a geometric mean, an arithmetic mean, a harmonic mean, an arithmetic geometric mean, an arithmetic harmonic mean, a geometric harmonic mean, a Pythagorean mean, an interquartile mean, a quadratic mean, a truncated mean, a winsorized mean, a weighted mean, a weighted geometric mean, a weighted arithmetic mean, a weighted harmonic mean, a mean of a function, a generalized mean, a generalized f-mean, a percentile, a maximum value, a minimum value, a mode, a median, a mid-range, a central tendency, a simple multiplication or a weighted multiplication, or by a functional operation of the calculated values, although not being limited thereto.

The drug score may be calculated by adjusting weightings of a target protein involved in the pharmacodynamics or pharmacokinetics of the corresponding drug, i.e., the anticancer agent, an enzyme protein involved in drug metabolism, a transporter protein or a carrier protein in consideration of pharmacological characteristics. The weighting may be assigned considering the pharmacokinetic parameters of the corresponding drug-metabolizing enzyme protein, a population group, a race distribution, etc. Further, although not directly interacting with the corresponding drug, proteins interacting with a precursor of the corresponding drug and metabolic products of the corresponding drug, for example, proteins involved in a pharmacological pathway, may be considered, and protein damage scores thereof may be combined to calculate the drug score. Further, protein damage scores of proteins significantly interacting with the proteins involved in the pharmacodynamics or pharmacokinetics of the corresponding drug may also be considered and combined to calculate the drug score. The information about the proteins involved in a pharmacological pathway of the corresponding drug, significantly interacting with the proteins in the pathway or involved in a signal transduction pathway thereof can be searched in publicly known biological databases such as PharmGKB (Whirl-Carrillo et al., *Clinical Pharmacology & Therapeutics* 2012; 92(4): 414-4171), The MIPS Mammalian Protein-Protein Interaction Database (Pagel et al., *Bioinformatics* 2005; 21(6): 832-834), BIND (Bader et al., Biomolecular Interaction Network Database, *Nucleic Acids Res.* 2003 Jan. 1; 31(1): 248-50), Reactome (Joshi-Tope et al., *Nucleic Acids Res.* 2005 Jan. 1; 33 (Database issue): D428-32), etc.

In an exemplary embodiment of the present disclosure, the drug score is calculated by Equation 3. The following Equation 3 can be modified in various ways, and, thus, the present disclosure is not limited thereto.

$$S_d(g_1,\ldots,g_n) = \left(\frac{1}{n}\sum_{i=1}^{n} g_i^p\right)^{\frac{1}{p}} \quad \text{[Equation 3]}$$

In Equation 3, $S_d$ is a drug score of a drug d, n is the number of proteins directly involved in the pharmacodynamics or pharmacokinetics of the drug d or interacting with a precursor of the corresponding drug or metabolic products of the corresponding drug, for example, proteins encoded by one or more gene selected from a gene group involved in a pharmacological pathway, $g_i$ is a protein damage score of a protein directly involved in the pharmacodynamics or pharmacokinetics of the drug d or interacting with a precursor of the corresponding drug or metabolic products of the corresponding drug, for example, a protein encoded by one or more gene selected from a gene group involved in a pharmacological pathway and p is a real number other than 0. In Equation 3, when the value of the p is 1, the drug score is an arithmetic mean, if the value of the p is −1, the drug score is a harmonic mean, and if the value of the p is close to the limit 0, the drug score is a geometric mean.

In another exemplary embodiment of the present disclosure, the drug score is calculated by Equation 4. The following Equation 4 can be modified in various ways, and, thus, the present disclosure is not limited thereto.

$$S_d(g_1,\ldots,g_n) = \left(\prod_{i=1}^{n} g_i^{\omega_i}\right)^{1/\sum_{i=1}^{n}\omega_i} \quad \text{[Equation 4]}$$

In Equation 4, $S_d$ is a drug score of a drug d, n is the number of proteins directly involved in the pharmacodynamics or pharmacokinetics of the drug d or interacting with a precursor of the corresponding drug or metabolic products of the corresponding drug, for example, proteins encoded by one or more gene selected from a gene group involved in a pharmacological pathway, $g_i$ is a protein damage score of a protein directly involved in the pharmacodynamics or pharmacokinetics of the drug d or interacting with a precursor of the corresponding drug or metabolic products of the corresponding drug, for example, a protein encoded by one or more gene selected from a gene group involved in a pharmacological pathway and $w_i$ is a weighting assigned to the $g_i$. If all the weightings $w_i$ have the same value, the drug score $S_d$ is a geometric mean of the protein damage scores $g_i$. The weighting may be assigned considering the kind of the protein, pharmacodynamic or pharmacokinetic classification of the protein, pharmacokinetic parameters of the enzyme protein of a corresponding drug, a population group or a race distribution.

In the case of a geometric mean calculation method used in an exemplary embodiment of the present disclosure, weightings are equally assigned regardless of the characteristic of a drug-protein relation. However, it is possible to calculate a drug score by assigning weightings considering each characteristic of a drug-protein relation as described in another exemplary embodiment. For example, different scores may be assigned to a target protein of a drug and a transporter protein related to the drug. Further, it is possible to calculate a drug score by assigning pharmacokinetic parameters $K_m$, $V_{max}$ and $K_{cat}/K_m$ as weightings to the corresponding drug-metabolizing enzyme. Furthermore, for example, since a target protein is regarded more important than a transporter protein in terms of pharmacological action, it may be assigned a higher weighting, or a transporter protein or a carrier protein may be assigned high weightings with respect to a drug whose effectiveness is sensitive to a concentration, but the present disclosure is not limited thereto. The weighting may be minutely adjusted according to the characteristics of a relation between a drug and a protein related to the drug and characteristics of an interaction between the drug and the protein. A sophisticated algorithm configured to assign a weighting of a characteristic of an interaction between a drug and a protein can be used. For example, a target protein and a transporter protein may be assigned 2 points and 1 point, respectively.

In the foregoing description, only the protein directly interacting with a drug, i.e., an anticancer agent, has been exemplified. However, the predictive ability of the above equations can be improved by using information about the protein interacting with a precursor of the corresponding drug or metabolic products of the corresponding drug, the protein significantly interacting with proteins involved in the pharmacodynamics or pharmacokinetics of the corresponding drug and the protein involved in a signal transduction pathway thereof. That is to say, by utilizing information about a protein-protein interaction network or pharmacological pathway, it is possible to use information about various proteins relevant thereto. That is to say, even if a significant variation is not found in the protein directly interacting with the drug so that there is no protein damage score calculated with respect to the protein or there is no damage (for example, 1.0 point when the SIFT algorithm is applied), a mean (for example, a geometric mean) of protein damage scores of proteins interacting with the protein or involved in the same signal transduction pathway of the protein may be used as a protein damage score of the protein so as to be used for calculating a drug score.

The individual drug score can be calculated with respect to all the drugs from which information about one or more associated proteins can be acquired or to some drugs selected from the drugs. Further, the individual drug score can be converted into a rank.

The method of the present disclosure may further include a step of determining whether the drug, i.e., the anticancer agent, will be used for the individual by using the above-described individual drug score.

Although the individual drug score can be applied to each of all drugs, it can be more useful when applied to drugs classified by disease, clinical characteristic or activity, or medically comparable drugs. The drug classification system which can be used in the present disclosure may include, for example, ATC (Anatomical Therapeutic Chemical Classification System) codes, a list of drugs with known pharmacogenomical markers which can influence the drug effect information described in the drug label, or a list of drugs withdrawn from the market due to side effects thereof, etc.

The method of the present disclosure may further include a step of calculating a prescription score.

The term "prescription score" used in the present disclosure refers to a score calculated by summarizing the drug scores determined with respect to drugs, respectively, when two or more drugs are administered at the same time or at a short distance of time sufficient to significantly affect pharmacological actions thereof. In the present disclosure, when two or more drugs are determined on the basis of the order of priority among drugs and need to be administered at the same time, the prescription score may be calculated by summarizing the drug scores determined with respect to the respective drugs. For example, if there is no protein commonly interacting with the drugs, the prescription score may be calculated by simply averaging, or summing up or multiplying drug scores of the drugs. If there is a protein commonly interacting with the drugs, the prescription score may be calculated by assigning, for example, a double weighting to a protein damage score of the corresponding commonly interacting protein to calculate drug scores of the respective drugs and then summing up the corresponding drug scores.

The prescription score is provided to determine the appropriateness or risk of the drugs included in a prescription applied to an individual beyond the effects of the respective drugs. In this aspect, the method of the present disclosure may further include a step of determining the appropriateness or risk of a prescription applied to an individual.

The method of the present disclosure may be performed for the purpose of preventing the side effects of an anticancer agent, although not being limited thereto.

FIG. 1 is a flowchart illustrating each step of a method for providing information for selecting an anticancer agent using individual genome sequence variation according to an exemplary embodiment of the present disclosure. In an exemplary embodiment of the present disclosure, the method for providing information for selecting an anticancer agent is performed by sequentially (1) inputting or receiving genome sequence information of an individual user (S100), (2) inputting or receiving information relevant to an anticancer agent (S110), (3) determining genome sequence variation information of the individual user (S120), (4) calculating an individual protein damage score with respect to the anticancer agent (S130), (5) calculating an individual drug score with respect to the anticancer agent (S140), (6) displaying the drug score and sorting drugs by ranking or determining the order of priority among drugs according to drug score rankings (S150) and (7) selecting an anticancer agent in consideration of the drug score and the priority and calculating a prescription score (S160).

The method of the present disclosure may further include a step of assisting a doctor in charge of prescription in making a decision by providing a pharmacogenomic calculation procedure and a ground for calculating the drug score as information in the form of a diagram, a chart, explanation, etc. when a drug score sorted by ranking as described above is selected. That is to say, the method according to the present disclosure may further include a step of providing one or more information among gene sequence variation information, a gene sequence variation score, a protein damage score, a drug score, and information used for calculation thereof.

In another aspect, the present disclosure relates to a system for selecting an anticancer agent using individual genome sequence variation, which includes: a database from which information relevant to a gene or protein related to an anticancer agent applicable to an individual can be searched or extracted; a communication unit which is accessible to the database; a first calculation module which is configured to calculate one or more gene sequence variation information involved in the pharmacodynamics or pharmacokinetics of the anticancer agent on the basis of the information; a second calculation module which is configured to calculate an individual protein damage score by using the gene sequence variation information; a third calculation module which is configured to calculate an individual drug score by associating the individual protein damage score with a drug-protein relation; and a display unit which is configured to display the values calculated by the calculation modules.

In the present disclosure, a module may mean a functional or structural combination of hardware for implementing the technical spirit of the present disclosure and software for driving the hardware. For example, the module may be a predetermined code and a logical unit of a hardware resource by which the predetermined code is executed. It is obvious to those skilled in the art that the module does not necessarily mean physically connected codes or one kind of hardware.

The term "calculation module" used in the present disclosure may mean a predetermined code and a logical unit of a hardware resource by which the predetermined code is executed for calculating each score on the basis of the gene sequence variation score, protein damage score, drug score, and information as grounds for calculation thereof with respect to an anticancer agent and a gene to be analyzed according to the present disclosure, but does not necessarily mean physically connected codes or one kind of hardware.

The system according to the present disclosure may further include a fourth calculation module which is configured to determine whether the anticancer agent is applicable to the individual by using the individual drug score calculated by the third calculation module.

The system according to the present disclosure may further include a fifth calculation module which is configured to calculate a prescription score by summarizing drug scores determined with respect to respective drugs if two or more drugs are determined on the basis of the order of priority among drugs and need to be administered at the same time.

The system according to the present disclosure may further include a user interface which is configured to input a list of anticancer agents by the user, or access a database containing information about anticancer agents and extract relevant information, and thereby calculate and provide a drug score of the drug.

The system according to the present disclosure may further include a display unit which is configured to display the values calculated by the respective calculation modules or a calculation process for determining the order of priority among drugs and information as a ground for the calculation or determination.

In the system according to the present disclosure, the database or a server including access information, the calculated information and the user interface connected thereto may be used as being linked to one another.

If new pharmacological/biochemical information regarding a drug-protein relation is produced, the system according to the present disclosure may be immediately updated so as to be used for further improved selection of an anticancer agent. In an exemplary embodiment of the present disclosure, when the database or knowledge base is updated, the gene sequence variation information, gene sequence variation score, protein damage score, drug score and the information as grounds for the calculation thereof stored in the respective calculation modules are updated.

FIG. 2 schematically illustrates the configuration of a system for selecting an anticancer agent using individual genome sequence variation according to an exemplary embodiment of the present disclosure. A system 10 of the present disclosure may include a database (DB) 100 from which information relevant to a gene or protein related to an anticancer agent can be searched or extracted, a communication unit 200, a user interface or terminal 300, a calculation unit 400 and a display unit 500.

In the system according to the present disclosure, the user interface or terminal 300 may be configured to request a processing for selecting an anticancer agent using individual genome sequence variations to a server and receive a result from a server and/or store it. The user interface or terminal 300 may consist of a terminal, such as a smart phone, a PC (personal computer), a tablet PC, a personal digital assistant (PDA) and a web pad, which includes a memory means and has a mobile communication function with a calculation ability using a microprocessor.

In the system according to the present disclosure, the server is a means for providing access to the database 100 with respect to an anticancer agent, a gene variation or a drug-protein relation and is connected to the user interface or terminal 300 through the communication unit 200 so as to exchange various kinds of information. Herein, the communication unit 200 may use any communication method regardless of whether it is wired or wireless, including not only communication in the same hardware but also a local area network (LAN), a metropolitan area network (MAN), a wide area network (WAN), the Internet, 2G, 3G and 4G mobile communication networks, Wi-Fi, Wibro, etc. The database 100 may be directly installed in the server and may also be connected to various life science databases accessible via the Internet depending on purposes.

In the system according to the present disclosure, the calculation unit 400 may include a first calculation module 410 which is configured to calculate one or more gene sequence variation information involved in the pharmacodynamics or pharmacokinetics of the anticancer agent using the collected/inputted information, a second calculation module 420 which is configured to calculate an individual protein damage score and a third calculation module which is 430 configured to calculate an individual drug score, as described above.

The method according to the present disclosure can be implemented by hardware, firmware, software or combinations thereof. When the method is implemented by software, a storage medium may include any storage or transmission medium readable by a device such as a computer. For example, the computer-readable medium may include a ROM (read only memory); a RAM (random access memory); a magnetic disc storage medium; an optical storage medium; a flash memory device; and other electric, optical or acoustic signal transmission medium.

In this aspect, the present disclosure provides a computer-readable medium including an execution module for executing a processor which performs an operation including: a step of acquiring one or more gene sequence variation information involved in the pharmacodynamics or pharmacokinetics of an anticancer agent from individual genome sequence information; a step of calculating an individual protein damage score using the gene sequence variation information; and a step of calculating an individual drug score by associating the individual protein damage score with a drug-protein relation.

The processor may further include a step of determining whether the anticancer agent will be used for the individual using the individual drug score processor.

In another aspect, the present disclosure provides a biomarker composition for predicting the side effect of an anticancer agent.

Genes that may be contained in the biomarker composition according to the present disclosure include ABCC1, ABCG2, APEX1, CBR3, ATP7A, CBR3, CTH, CUL9, CYP1A1, CYP2C9, CYP2D6, CYP4B1, DPEP1, DPEP2, DPYD, DRD3, EPHX1, FMO2, FMO3, GGT1, GGT5, GGT6, GNB3, GSTA2, GSTM1, MGMT, MLH1, MSH2, NAT1, OPRM1, PDE5A, PTGS1, SERPINA6, SLC15A2, SLC22A1, SLC22A2, SLC22A8, SLC22A16, SLC28A2, SLC28A3, SPG7, TP53, ABCB1, ABCC2, AOX1, CHRM2, CYP1B1, CYP3A4, CYP3A5, CYP4F2, DBH, ERCC2, GGH, GGT7, GMPS, MTHFR, NUDT15, PDE3A, PDE4C, SLC22A5, SLCO1B1, TLR3, UGT1A1, XDH, etc., although not being limited thereto. Because the onset of a side effect of an anticancer agent can be predicted by analyzing variations of these genes or their proteins, an agent capable of detecting them may be used as a marker.

Hereinafter, the present disclosure will be described in detail through examples. However, the following examples are for illustrative purposes only and the scope of the present disclosure is not limited by the examples.

Example 1

Analysis and Application of Individual Genome Sequence Variation Information of Pediatric Leukemia Patients Showing Warning Skins of Serious Side Effects During Treatment with Anticancer Agent (Busulfan)

Bone marrow transplantation is one of the most important treatment methods for treating blood tumor such as leukemia. For bone marrow transplantation, the bone marrow of a patient needs to be removed first by using two methods: total body irradiation (TBI) and pharmacological treatment using drugs such as busulfan. Busulfan is a representative alkylating agent and can replace the total body irradiation. However, it has a relatively narrow therapeutic range. If the drug concentration is higher than the therapeutic range, hepatic veno-occlusive disease (VOD) and severe toxicity, such as neurotoxicity, relevant to the drug occurs. And, if the drug concentration is lower than the therapeutic range, the likelihood of graft failure or relapse is increased. Particularly, children show great differences in the pharmacokinetics of busulfan among individuals. Therefore, busulfan is used under therapeutic drug monitoring (TDM). The toxicity of busulfan includes interstitial pulmonary fibrosis commonly called "busulfan Lung", hyperpigmentation, epilepsy, veno-occlusive disease (VOD), nausea, thrombocytopenia, etc. The IARC (International Agency for Research on Cancer) classifies busulfan as one of Group 1 carcinogens.

In order to check whether it is possible to identify a risk group with respect to the busulfan treatment through the method for providing information for selecting an anticancer agent using individual genome sequence variations of the present disclosure, the following experiment was conducted.

Firstly, an analysis was conducted on 146 pediatric leukemia patients showing warning signs of serious side effects during treatment with the anticancer agent busulfan (Myleran, GlaxoSmithKline, Busulfex IV, Otsuka America Pharmaceutical, Inc.) to remove bone marrow as a preconditioning for bone marrow transplantation. Among the 146 patients, 124 showed malignant blood tumors. The side effect profile of the 146 patients is given in Table 2.

TABLE 2

| No. | Side effects | Number of patients |
| --- | --- | --- |
| 1 | Toxicity-related death | 22 |
| 2 | Intermediate toxicity grade 3 or higher | 11 |
| 3 | Intermediate toxicity grade 4 or higher | 1 |
| 4 | Short-term toxicity grade 3 or higher | 31 |
| 5 | Short-term toxicity grade 4 or higher | 2 |
| 6 | Hepatic veno-occlusive disease | 18 |
| 7 | Death | 36 |
| 8 | AUC 170 or higher | 71 |

280× targeted exome sequencing was conducted using Ion Proton (Life Technology) in order to acquire the individual genome sequence variation information of the 146 patients. Alternatively, whole genome sequencing of acquiring the information of the whole individual genome or whole exome sequencing of acquiring the information of the genes encoding proteins may be conducted.

The analyzed sequence fragments underwent data cleaning and quality checking and outputted in the form of SAM (Sequence Alignment Map) and BAM (Binary Alignment Map) files aligned with a human reference group sequence (e.g., HG19). The cleaned alignment result was outputted in the form of VCF (Variation Calling Format) file while detecting variations such as single nucleotide variations (SNVs) and Indels by using software tools such as SAMTools:pileup, SAMTools:mpileup, GATK:recalibration, GATK:realignment, and the like.

After the VCF file including the gene sequence variation information was inputted and the above-described gene sequence variation score $v_i$ was calculated for each variant, an individual protein damage score $S_g$ was calculated using Equation 2. Then, after comparing the protein damage score of patient groups showing different side effects with the protein damage score of the control group, 48 genes showing statistically significant difference for the respective side effects were selected as follows. Among them, 28 genes showing higher statistical significance based on the p-value were classified as group 1. The following genes are those showing high relevance to the pharmacodynamics or pharmacokinetics of busulfan and its metabolic products.

Group 1

ABCC1, ABCG2, ATP7A, CBR3, CTH, CUL9, CYP1A1, CYP2C9, DPEP1, DPEP2, DPYD, DRD3, FMO2, GGT1, GGT5, GGT6, GSTA2, GSTM1, MSH2, NAT1, PDE5A, PTGS1, SLC15A2, SLC22A1, SLC22A16, SLC22A2, SLC28A2, SPG7

Group 2

ABCB1, ABCC2, AOX1, CHRM2, CYP1B1, CYP2D6, CYP3A4, DBH, EPHX1, GGT7, GMPS, MTHFR, PDE3A, PDE4C, SERPINA6, SLC22A5, SLC22A8, TLR3, TP53, UGT1A1

For the selected gene groups, the individual drug score was calculated for the 146 pediatric leukemia patients using the method of the present disclosure. More specifically, after calculating the gene sequence variation score from the individual gene sequence variation information using the SIFT algorithm, the individual protein damage score was calculated for the 48 genes using Equation 2. Then, after calculating the individual drug score for busulfan using Equation 4, statistical analysis was conducted for each group. The protein damage score distribution of the busulfan side effect positive group and negative group is shown in Table 3.

TABLE 3

|  | Busulfan side effect positive group (n = 90) | Busulfan side effect negative group (n = 56) | p-value |
|---|---|---|---|
| Mean drug score (group 1 drug) | 0.195406408 | 0.468837374 | 0.072382486 |
| Mean drug score (group 1 & 2 drugs) | 0.273943475 | 0.5030009 | 0.034605505 |
| Group 1 protein damage score | | | |
| SLC22A16 | 0.3236 ± 0.01 | 0.55 ± 0.33 | 2.03E-13 |
| CBR3 | 0.0829 ± 0.04 | 0.185 ± 0.16 | 2.83E-07 |
| FMO2 | 1.0E-8 ± 0 | 0.1556 ± 0.36 | 1.01E-06 |
| PTGS1 | 0.3744 ± 0.01 | 0.4543 ± 0.21 | 1.07E-05 |
| SLC15A2 | 0.1114 ± 0.04 | 0.2232 ± 0.32 | 0.000400521 |
| DRD3 | 0.54 ± 0 | 0.5809 ± 0.15 | 0.001222641 |
| SLC22A2 | 0.1 ± 0 | 0.1625 ± 0.23 | 0.001367927 |
| GGT6 | 0.0578 ± 0.01 | 0.0635 ± 0.01 | 0.001375077 |
| CUL9 | 0.8383 ± 0.36 | 0.962 ± 0.19 | 0.005778935 |
| GSTA2 | 0.458 ± 0.17 | 0.5249 ± 0.15 | 0.006675864 |
| SPG7 | 0.6653 ± 0.34 | 0.8593 ± 0.27 | 0.009214375 |
| CYP1A1 | 0.2903 ± 0.43 | 0.4599 ± 0.48 | 0.013394813 |
| GGT1 | 0.1 ± 0.29 | 0.2655 ± 0.43 | 0.014831285 |
| ABCC1 | 0.432 ± 0.26 | 0.5392 ± 0.3 | 0.020942712 |
| DPEP1 | 0.529 ± 0.37 | 0.6555 ± 0.38 | 0.0220818 |
| ATP7A | 0.5597 ± 0.46 | 0.7468 ± 0.41 | 0.023348076 |
| GGT5 | 0.2332 ± 0.3 | 0.4314 ± 0.41 | 0.029370818 |
| GSTM1 | 0.8037 ± 0.35 | 0.9016 ± 0.27 | 0.03104692 |
| SLC22A1 | 0.4535 ± 0.3 | 0.5463 ± 0.29 | 0.031693911 |
| DPEP2 | 0.8528 ± 0.33 | 0.9597 ± 0.19 | 0.037121203 |
| CTH | 0.48 ± 0.44 | 0.6665 ± 0.43 | 0.0389814 |
| PDE5A | 0.2971 ± 0.03 | 0.3213 ± 0.11 | 0.040084719 |
| DPYD | 0.1675 ± 0.04 | 0.2002 ± 0.16 | 0.043865116 |
| ABCG2 | 0.4891 ± 0.34 | 0.6836 ± 0.35 | 0.045862428 |
| CYP2C9 | 0.9679 ± 0.16 | 1 ± 0 | 0.046448221 |
| SLC28A2 | 0.7307 ± 0.39 | 0.8613 ± 0.31 | 0.047310042 |
| MSH2 | 0.7484 ± 0.43 | 0.8897 ± 0.3 | 0.048069264 |
| NAT1 | 0.9433 ± 0.13 | 0.9973 ± 0.03 | 0.048855771 |
| Group 2 protein damage score | | | |
| SERPINA6 | 0.0822 ± 0.04 | 0.1017 ± 0.09 | 0.050821316 |
| EPHX1 | 0.1653 ± 0.28 | 0.3055 ± 0.43 | 0.05389215 |
| GMPS | 0.6267 ± 0.43 | 0.8031 ± 0.36 | 0.055682706 |
| CYP2D6 | 0.1833 ± 0.38 | 0.3415 ± 0.46 | 0.058740693 |
| MTHFR | 0.1745 ± 0.28 | 0.2669 ± 0.37 | 0.066912194 |
| ABCC2 | 0.6567 ± 0.4 | 0.8253 ± 0.33 | 0.068738095 |
| TLR3 | 0.314 ± 0.47 | 0.5634 ± 0.49 | 0.069997413 |
| AOX1 | 0.6036 ± 0.47 | 0.8249 ± 0.34 | 0.076843585 |
| GGT7 | 0.9765 ± 0.13 | 1 ± 0 | 0.079490244 |
| CHRM2 | 0.9763 ± 0.14 | 1 ± 0 | 0.07962271 |
| SLC22A8 | 0.5261 ± 0.32 | 0.6255 ± 0.34 | 0.080067267 |
| CYP3A4 | 0.9589 ± 0.17 | 0.9903 ± 0.08 | 0.081583332 |
| DBH | 0.7415 ± 0.31 | 0.8303 ± 0.27 | 0.081601181 |
| UGT1A1 | 0.5425 ± 0.47 | 0.6935 ± 0.44 | 0.085536737 |
| CYP1B1 | 0.242 ± 0.08 | 0.2681 ± 0.13 | 0.088335873 |
| PDE4C | 0.6012 ± 0.48 | 0.7217 ± 0.44 | 0.0936022 |
| TP53 | 0.2161 ± 0.2 | 0.2867 ± 0.29 | 0.095578636 |
| PDE3A | 0.4937 ± 0.18 | 0.5406 ± 0.15 | 0.097645758 |
| SLC22A5 | 0.9283 ± 0.25 | 0.9824 ± 0.13 | 0.107609865 |
| ABCB1 | 0.7691 ± 0.38 | 0.8404 ± 0.35 | 0.210600695 |

As seen from Table 3, statistically significant difference was observed between the busulfan side effect positive group (n=90) and the busulfan side effect negative group (n=56) when the protein damage score and the individual drug score were calculated from the gene sequence variation information using the selected 28 genes of the group 1 (p-value<0.05).

Also, when the individual drug score was calculated from the gene sequence variation by further including the genes of the group 2, statistically significant difference was observed between the two groups (p-value<0.05).

Through these results, it was demonstrated that it is possible to significantly distinguish a group showing warning signs of serious side effects during treatment with busulfan (risk group) from a non-risk group by calculating the individual drug scores through analysis of individual genome sequence variation information according to the present disclosure and it is possible to prevent unwanted side effects.

With the above-described result, it is possible to predict a group with a high likelihood of side effects when busulfan is administered to a pediatric leukemia patient, according to the method of the present disclosure, and it is also possible to adjust the drug concentration or use an alternative treatment method or interventional method for a high-risk group.

Example 2

Analysis and Application of Individual Genome Sequence Variation Information of Leukemia Patients Showing Leukopenia and Liver Toxicity During Treatment with Anticancer Agent (Mercaptopurine)

Mercaptopurine is used together with other drugs for maintenance therapy in the treatment of acute lymphocytic leukemia. Mercaptopurine is metabolized in the body and converted to thioguanine nucleotides (TGNs), which exhibit anticancer effect by inhibiting DNA synthesis. Mercaptopurine is metabolized by thiopurine S-methyltransferase. When the patient has variation in the TPMT gene which encodes the protein, serious life-threatening side effects such as leukopenia, agranulocytosis or liver toxicity may occur. In particular, when the patient has variation of the TPMT gene on both alleles, life-threatening bone marrow suppression may occur. And, even when the variation of the TPMT gene occurs on only one allele, higher toxicity and bone marrow suppression are observed as compared to when both alleles are normal.

Recently, from a study on Asians patients who have normal TPMT genes but show the toxicity and bone marrow suppression described above, the relationship between the NUDT15 gene and the thiopurine-based drug was elucidated. In one prospective cohort study (Yang, J. J., Landier, W., Yang, W., Liu, C., Hageman, L., Cheng, C., . . . & Wong, F. L. (2015). Inherited NUDT15 variant is a genetic determinant of mercaptopurine intolerance in children with acute lymphoblastic leukemia. *Journal of Clinical Oncology*, JCO-2014.), it was confirmed through whole genome sequencing that rs1142345, a SNP of the TPMT gene, and rs116855232, a SNP of the NUDT15 gene, are associated with the dose of mercaptopurine maintenance therapy. From comparison of the therapeutic dose of mercaptopurine, it was found out that the therapeutic dose was decreased when the SNPs were present. Because doctors lower the therapeutic dose when severe toxicity occurs during treatment, it can be seen that the SNPs are highly related with the occurrence of toxicity during the treatment.

In order to investigate whether a risk group can be identified in mercaptopurine treatment using the method for providing information for selecting an anticancer agent using individual genome sequence variation of the present disclosure, the following experiment was conducted.

A patient group to which mercaptopurine treatment was given for about 2 years was analyzed. The side effect profile of the patient group is given in Table 4.

TABLE 4

| No. | Side effects |
| --- | --- |
| 1 | Neutropenic fever |
| 2 | ANC < 500 |
| 3 | Hyperbilirubinemia of grade 3 or higher |
| 4 | Liver toxicity (GOT) of grade 2 or higher |
| 5 | Liver toxicity (GPT) of grade 3 or higher |
| 6 | Liver toxicity of grade 3 or higher in neutropenia group |

280× targeted exome sequencing was conducted using Ion Proton (Life Technology) in order to acquire the individual genome sequence variation information of the patient group. Alternatively, whole genome sequencing of acquiring the information of the whole individual genome or whole exome sequencing of acquiring the information of the genes encoding proteins may be conducted.

The analyzed sequence fragments underwent data cleaning and quality checking and outputted in the form of SAM (Sequence Alignment Map) and BAM (Binary Alignment Map) files aligned with a human reference group sequence (e.g., HG19). The cleaned alignment result was outputted in the form of VCF (Variation Calling Format) file while detecting variations such as single nucleotide variations (SNVs) and Indels by using software tools such as SAMTools:pileup, SAMTools:mpileup, GATK:recalibration, GATK:realignment, and the like.

After the VCF file including the gene sequence variation information was inputted and the above-described gene sequence variation score $v_i$ was calculated for each variant, an individual protein damage score $S_g$ was calculated using Equation 2. Then, after comparing the protein damage score of patient groups showing different side effects with the protein damage score of the control group, 32 genes showing statistically significant difference were selected as follows. Among them, the genes showing higher statistical significance based on the p-value were classified as group 1. The following genes are those showing high relevance to the pharmacodynamics or pharmacokinetics of mercaptopurine and its metabolic products.

Group 1

ABCC1, APEX1, CBR3, CUL9, CYP2D6, CYP4B1, DPEP1, DPYD, EPHX1, FMO3, GNB3, MGMT, MLH1, OPRM1, PDE5A, SERPINA6, SLC15A2, SLC22A2, SLC22A8, SLC28A3, TP53

Group 2

CHRM2, CYP1B1, CYP3A5, CYP4F2, ERCC2, FMO2, GGH, NUDT15, PDE4C, SLCO1B1, XDH

For the selected gene groups, the individual drug score was calculated using the method of the present disclosure. More specifically, after calculating the gene sequence variation score from the individual gene sequence variation information using the SIFT algorithm, the individual protein damage score was calculated for the 32 genes using Equation 2. Then, after calculating the individual drug score for 6-mercaptopurine using Equation 4, statistical analysis was conducted for each group. The protein damage score distribution of the 6-mercaptopurine side effect positive group and negative group is shown in Table 5.

TABLE 5

|  |  | Mercaptopurine side effect positive group (n = 6) | Mercaptopurine side effect negative group (n = 34) | p-value |
| --- | --- | --- | --- | --- |
| Mean drug score (group 1 drug) | | 0.1034 ± 0.09 | 0.1890 ± 0.10 | 0.024589877 |
| Mean drug score (group, 1 & 2 drugs) | | 0.0934 ± 0.05 | 0.1749 ± 0.09 | 0.021586521 |
| Protein damage score (group 1) | DPEP1 | 0.24 ± 0 | 0.7741 ± 0.35 | 2.56E−11 |
| | ABCC1 | 0.32 ± 0 | 0.5316 ± 0.32 | 0.000147391 |
| | MGMT | 0.7706 ± 0.36 | 1 ± 0 | 0.000382075 |
| | SLC22A8 | 0.3166 ± 0.01 | 0.5166 ± 0.32 | 0.000416193 |
| | CYP2D6 | 0.018 ± 0 | 0.2319 ± 0.41 | 0.00151514 |
| | EPHX1 | 1.0E−8 ± 0 | 0.1957 ± 0.39 | 0.001937214 |
| | APEX1 | 0.8209 ± 0.36 | 1 ± 0 | 0.003093326 |
| | CYP4B1 | 0.7962 ± 0.41 | 1 ± 0 | 0.003093326 |
| | CUL9 | 0.8047 ± 0.39 | 1 ± 0 | 0.003148978 |
| | MLH1 | 0.8418 ± 0.36 | 1 ± 0 | 0.007651081 |
| | TP53 | 0.17 ± 0 | 0.2822 ± 0.29 | 0.011587433 |
| | OPRM1 | 0.3747 ± 0.49 | 0.7171 ± 0.46 | 0.01443295 |
| | PDE5A | 0.3 ± 0 | 0.3043 ± 0.01 | 0.016470184 |
| | SERPINA6 | 0.07 ± 0 | 0.1147 ± 0.12 | 0.01668446 |
| | FMO3 | 0.2853 ± 0.35 | 0.6381 ± 0.38 | 0.01974977 |
| | DPYD | 0.18 ± 0 | 0.2765 ± 0.27 | 0.021839396 |
| | SLC15A2 | 0.1215 ± 0.06 | 0.2519 ± 0.34 | 0.029659527 |
| | CBR3 | 0.0993 ± 0.1 | 0.1811 ± 0.1 | 0.039359969 |
| | SLC28A3 | 0.8103 ± 0.3 | 0.9569 ± 0.2 | 0.039421696 |
| | GNB3 | 0.9126 ± 0.29 | 1 ± 0 | 0.041559264 |
| | SLC22A2 | 0.1 ± 0 | 0.1794 ± 0.26 | 0.041559264 |
| Protein damage score ((group 2) | XDH | 0.9471 ± 0.19 | 1 ± 0 | 0.057393496 |
| | FMO2 | 0.125 ± 0.34 | 0.3333 ± 0.48 | 0.058959933 |
| | CYP1B1 | 0.1775 ± 0.09 | 0.2415 ± 0.1 | 0.063676645 |
| | SLCO1B1 | 0.4394 ± 0.36 | 0.5998 ± 0.3 | 0.075169523 |
| | CHRM2 | 0.9482 ± 0.21 | 1 ± 0 | 0.080187516 |
| | ERCC2 | 0.9547 ± 0.18 | 1 ± 0 | 0.080187516 |
| | GGH | 0.9518 ± 0.2 | 1 ± 0 | 0.080187516 |
| | CYP3A5 | 0.9435 ± 0.23 | 1 ± 0 | 0.080374542 |
| | CYP4F2 | 0.175 ± 0.4 | 0.4468 ± 0.5 | 0.0910071 |
| | PDE4C | 0.4343 ± 0.53 | 0.7454 ± 0.44 | 0.092029759 |
| | NUDT15 | 0.48 ± 0.49 | 0.7646 ± 0.41 | 0.093049258 |

As seen from Table 5, statistically significant difference was observed between the mercaptopurine side effect positive group (n=6) and the mercaptopurine side effect negative group (n=34) when the protein damage score and the individual drug score were calculated from the gene sequence variation information using the genes of the group 1 (p-value<0.05).

Also, when the individual drug score was calculated from the gene sequence variation by further including the genes of the group 2, statistically significant difference was observed between the two groups.

Through these results, it was demonstrated that it is possible to significantly distinguish a group showing warning signs of serious side effects during treatment with mercaptopurine (risk group) from a non-risk group by calculating the individual drug scores through analysis of individual genome sequence variation information according to the present disclosure and it is possible to prevent unwanted side effects.

With the above-described result, it is possible to predict a group with a high likelihood of side effects when mercaptopurine is administered to a patient, according to the method of the present disclosure, and it is also possible to adjust the drug concentration or use an alternative treatment method or interventional method for a high-risk group.

Example 3

Demonstration of Validity of Method for Personalizing Drug Selection Based on Individual Genome Sequence Variation Information Reliable study results about individual genome sequence variation information and an individual difference in pharmacodynamics response have been very limited so far. The studies conducted thus far have followed a paradigm of a case-control study in which an individual difference in responsiveness is studied by comparing a group with a specific variation with a group without the specific variation for each drug. In this study paradigm, a costly case-control study needs to be conducted for each of all combinations of pairs of numerous sequence variants and numerous drugs, which is practically impossible. In contrast, the method for personalizing drug selection according to the present disclosure is applicable to all gene sequence without requiring a costly case-control study. The present disclosure provides a method which can calculate an individual protein damage score and an individual drug score just by calculating a genome sequence variation. Therefore, the method has an advantage of being able to make a deduction for personalizing drug selection with respect to combinations between all genome sequence variations and all drugs.

In order to evaluate the validity of a result of personalized drug selection according to the method of the present disclosure, 497 frequently prescribed drugs were selected on the basis of the following criteria: (1) drugs, of which at least one gene involved in the pharmacodynamics or pharmacokinetics is known, among drugs included in the ATC codes of top 15 frequently prescribed drug classes during 2005 to 2008 in the United States (Health, United States, 2011, Centers for Disease Control and Prevention), (2) drugs with information on the established effects of pharmacogenomic genome sequence variation markers in US FDA drug labels, and (3) drugs disclosed in the database of DrugBank as having been withdrawn from the market due to drug side effects.

As data for evaluating the validity, among the established knowledge about 987 gene sequence variation-drug interaction pairs provided by PharmGKB, 650 pairs (65.9%) having at least one link to the 497 drugs were extracted. Considering that the target of the present disclosure is a sequence variation in an exon region, the overlapping part between data of the verification target and data of the evaluation standard were removed for a fair evaluation. To be more specific, a fairer evaluation was conducted by removing the pairs with all of 36 sequence variations positioned in the exon region among the 650 pairs and selecting only a sequence variation in a non-coding region. As a result, 614 pairs were selected as a final gold standard for evaluation.

Then, the whole genome sequences of 1092 persons provided by the 1000 Genomes Project were analyzed, and the method according to the present disclosure was applied to each of the 1092 persons to thereby calculate individual pharmacogenomic risk and pharmacogenomic risk of each gene sequence variation registered at PharmGKB.

For the validity evaluation, sensitivity, specificity and an area under the receiver operating characteristic (ROC) curve were used. The 497 drugs were ranked on the basis of individual drug scores and threshold values were set for each ranking at 496 segment positions between the ranks. Then, (1) when a ranking of a drug score of a corresponding drug was higher than a threshold and a PharmGKB variation was present in an individual genome variation, it was determined as true positive, (2) when a ranking of a drug score of a corresponding drug was lower than a threshold and a PharmGKB variation was not present in an individual genome variation, it was determined as true negative, (3) when a ranking of a drug score of a corresponding drug was higher than a threshold but a PharmGKB variation was not present in an individual genome variation, it was determined as false positive, and (4) when a ranking of a drug score of a corresponding drug was lower than a threshold but a PharmGKB variation was present in an individual genome variation, it was determined as false negative. The numbers of true positive, true negative, false positive, and false negative cases of each individual with respect to each ranking threshold L were calculated, and the sensitivity and the specificity were calculated according to the following equations.

Sensitivity=$|D_L \cap GS|/|GS|$

Specificity=$1-\{|D_L-GS|/|D-GS|\}$

In the above equations, D is a set of all the 497 drugs, GS is a set of personalized PharmGKB drugs used as an individual gold standard since an individual gene sequence variation in each individual is identical with a risk allele of PharmGKB, $D_L$ is a set of drugs with high ranking thresholds, and the vertical bar parenthesis means the number of elements of the corresponding set.

As a result of the calculation, 18 persons had no variation identical to the variation of PharmGKB, and, thus, a set of personalized PharmGKB drugs used as an individual gold standard could not be defined. Therefore, the 18 persons were excluded from this validity test. The sensitivity and specificity were calculated with respect to all of the thresholds to draw the ROC curve and calculate the AUC. To be more specific, the gene sequence variation scores of the 1092 persons in the total population group were calculated using the SIFT algorithm, and then, protein damage scores and drugs scores were calculated using Equation 2 and Equation 4, respectively. Further, in order to determine the usefulness of application of weightings according to a race distribution, race-specific sensitivity and specificity and a value of AUC based on the sensitivity and specificity were calculated in the same manner for each of four races (African (AFR, n=246), American (AMR, n=181), Asian (ASN, n=286), European (EUR, n=379)) clearly stated in the 1000 Genomes Project, so that race-specific sensitivity and specificity and an AUC were obtained. The results are as listed in Table 6, Table 7 and FIG. 3.

TABLE 6

Distribution of protein group and mean protein damage score

| Protein group | Number of proteins | Number of relevant drugs | Number of protein-drug pairs | Mean protein damage score |
|---|---|---|---|---|
| Target protein | 440 | 486 | 2357 | 0.798 |
| Carrier protein | 10 | 50 | 65 | 0.728 |
| Enzyme protein | 74 | 330 | 1347 | 0.733 |
| Transporter protein | 54 | 176 | 457 | 0.733 |
| Total | 545 | 497 | 4201 | 0.783 |

TABLE 7

Validity (AUC) of drug score calculated for each protein group and each race using the 1000 Genomes Project data

| | Total | AFR | AMR | ASN | EUR |
|---|---|---|---|---|---|
| Validity of drug score calculation (AUC) | | | | | |
| Target protein | 0.617 | 0.634 | 0.608 | 0.614 | 0.614 |
| Carrier protein | 0.554 | 0.511 | 0.599 | 0.485 | 0.594 |
| Enzyme protein | 0.587 | 0.642 | 0.580 | 0.558 | 0.579 |
| Transporter protein | 0.497 | 0.492 | 0.488 | 0.489 | 0.512 |
| Validity of drug score calculation drug score with or without weighting to each applied protein group (AUC) | | | | | |
| Simple geometric mean | 0.666 | 0.744 | 0.650 | 0.634 | 0.653 |
| Weighted geometric mean | 0.667 | 0.742 | 0.652 | 0.633 | 0.654 |

Table 6 lists the distribution of proteins relating to the 497 drugs used in this example for each protein group, and indicates the number of protein-drug pairs together with a mean protein damage score for each group.

Table 7 lists the validity of individual drug score calculation (AUC) respectively calculated in the case where weightings are not applied to each protein group (simple geometric mean) and the case where weightings are applied to each protein group (weighted geometric mean) when calculating the drug score using Equation 4 with respect to each protein group and each race.

More specifically, for example, in the total population group, the AUC values calculated for protein groups such as target proteins, carrier proteins, metabolism enzyme proteins and transporter enzymes were 0.617, 0.554, 0.587, and 0.497, respectively. These values were used as weightings for the respective protein groups (each value was substituted for the weighting $w_i$ of Equation 4) to thereby obtain the validity of individual drug score calculation using weighted geometric mean (AUC=0.667) (see FIG. 3B). As a result, it was confirmed that the validity of individual drug score calculation using weighted geometric mean in the case of assigning the weightings for the respective protein groups were increased by 0.001 point as compared with the validity of individual drug score calculation using simple geometric mean (AUC=0.666) calculated by applying a simple geometric mean calculation formula without assigning a weighting (weighting $w_i$=1) (see FIG. 3A).

Also, as seen from FIG. 3A, as another example of applying weightings, weightings were assigned according to the number of people per race and the validity of individual drug score calculation (AUC) was analyzed. As a result, in the case of considering race specificity (bold line), the AUC value of the total population group (Total) was 0.666 (African: 0.744, American: 0.650, Asian: 0.631, and European: 0.653), and in the case of not considering the race specificity (dotted line), the AUC value of the total population group was 0.633 (African: 0.623, American: 0.629, Asian: 0.64, and European: 0.636). Accordingly, it was confirmed that the validity of individual drug score calculation in the case of considering the race specificity was improved as compared with the case of not considering the race specificity.

Figure 3B:
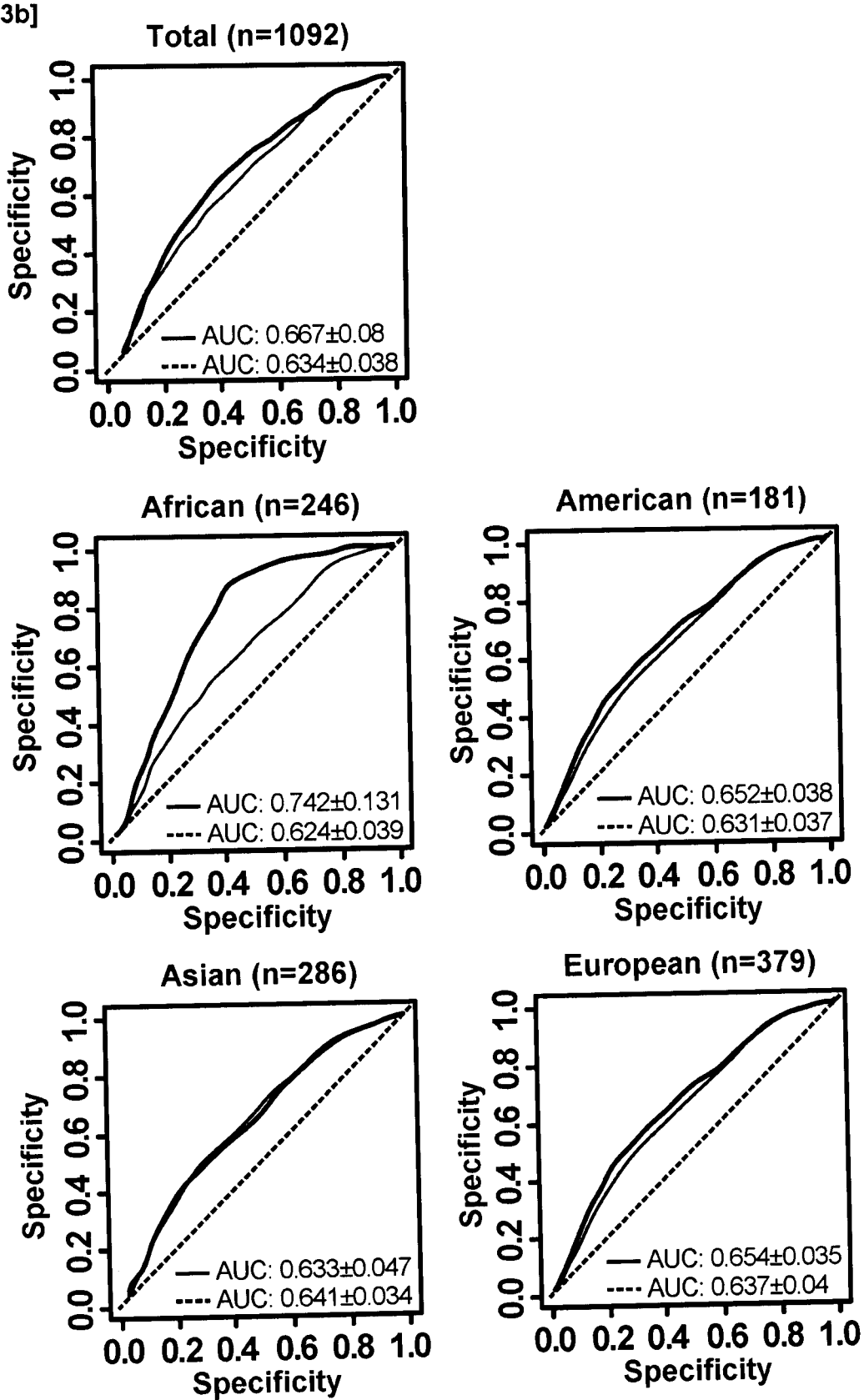

Further, as illustrated in FIG. 3B, in the case of assigning weightings for the respective protein groups without considering race specificity (dotted line), the validity of individual drug score calculation (AUC) of the present disclosure was 0.634, and in the case of assigning weightings for the respective protein groups while considering the race specificity (bold line), the validity of individual drug score calculation (AUC) of the present disclosure was 0.667. Accordingly, it can be seen that different weightings are useful.

Although the exemplary embodiments of the present disclosure have been described in detail, the scope of the present disclosure is not limited thereto. Various modifications and improvements made by those skilled in the art using the basic concept of the present disclosure defined in the appended claims are also included in the scope of the present disclosure.

Unless defined otherwise, all the technical terms used herein have the same meaning as those commonly understood by one of ordinary skill in the art to which this invention pertains. All the publications cited as references in the present specification are incorporated herein by reference in their entirety.

The invention claimed is:

1. A method for providing information for selecting an anticancer agent using individual genome sequence variation, the method comprising:

determining gene sequence variation information of one or more genes involved in pharmacodynamics or pharmacokinetics of an anticancer agent from individual genome sequence information;

calculating a gene sequence variation score using the gene sequence variation information, the gene sequence variation score being a numerical score indicating a degree of variation in one of the one or more genes that causes an amino acid sequence variation in a protein encoded by the gene or causes a transcription control variation, thereby causing change or damage to a structure or function of the protein;

calculating an individual protein damage score using [Equation 2], wherein [Equation 2] is $$S_g(v_1, \ldots, v_n) = \left(\prod_{i=1}^{n} v_i^{w_i}\right)^{\frac{1}{\sum_{i=1}^{n} w_i}}$$

wherein $S_g$ is a protein damage score of a protein encoded by a gene g, n is the number of target sequence variations to be analyzed among sequence variations of the gene g, $v_i$ is a gene sequence variation score of an i-th sequence variation and $w_i$ is a weighting assigned to the gene sequence variation score $v_i$ of the i-th sequence variation;

calculating an individual drug score using [Equation 4], wherein [Equation 4] is:

$$S_d(g_1, \ldots, g_n) = \left(\prod_{i=1}^{n} g_i^{w_i}\right)^{\frac{1}{\sum_{i=1}^{n} w_i}}$$

wherein $S_d$ is a drug score of a drug d, n is the number of proteins encoded by one or more genes involved in the pharmacodynamics or pharmacokinetics of the drug d, $g_i$ is a protein damage score of a protein encoded by one or more genes involved in the pharmacodynamics or pharmacokinetics of the drug d and $w_i$ is a weighting assigned to the protein damage score $g_i$ of the protein encoded by one or more genes involved in the pharmacodynamics or pharmacokinetics of the drug d; and providing the individual drug score for use in drug selection among anticancer agents.

2. The method for providing information for selecting an anticancer agent using individual genome sequence variation according to claim 1, wherein the anticancer agent is one or more selected from a group consisting of a thiopurine-based drug and a deoxynucleoside analog.

3. The method for providing information for selecting an anticancer agent using individual genome sequence variation according to claim 1, wherein the one or more genes involved in the pharmacodynamics or pharmacokinetics are one or more selected from a group consisting of ABCC1, ABCG2, APEX1, CBR3, ATP7A, CBR3, CTH, CUL9, CYP1A1, CYP2C9, CYP2D6, CYP4B1, DPEP1, DPEP2, DPYD, DRD3, EPHX1, FMO2, FMO3, GGT1, GGT5, GGT6, GNB3, GSTA2, GSTM1, MGMT, MLH1, MSH2, NAT1, OPRM1, PDE5A, PTGS1, SERPINA6, SLC15A2, SLC22A1, SLC22A2, SLC22A8, SLC22A16, SLC22A2, SLC28A2, SLC28A3, SPG7, TP53, ABCB1, ABCC2, AOX1, CHRM2, CYP1B1, CYP3A4, CYP3A5, CYP4F2, DBH, ERCC2, GGH, GGT7, GMPS, MTHFR, NUDT15, PDE3A, PDE4C, SLC22A5, SLCO1B1, TLR3, UGT1A1 and XDH.

4. The method for providing information for selecting an anticancer agent using individual genome sequence variation according to claim 1, wherein the gene sequence variation information is substitution, addition or deletion of a base constituting an exon of a gene.

5. The method for providing information for selecting an anticancer agent using individual genome sequence variation according to claim 1, wherein the gene sequence variation information is acquired by a comparison analysis with a genome sequence of a reference group.

6. The method for providing information for selecting an anticancer agent using individual genome sequence variation according to claim 1, wherein the protein damage score or the drug score is calculated from one or more gene sequence variation scores calculated using one or more algorithms selected from a group consisting of SIFT (Sorting Intolerant From Tolerant), PolyPhen (Polymorphism Phenotyping), PolyPhen-2, MAPP (Multivariate Analysis of Protein Polymorphism), Logre (Log R Pfam E-value), MutationAssessor, MutationTaster, MutationTaster2, PROVEAN (Protein Variation Effect Analyzer), PMut, Condel, GERP (Genomic Evolutionary Rate Profiling), GERP++, CEO (Combinatorial Entropy Optimization), SNPeffect, fathmm and CADD (Combined Annotation-Dependent Depletion).

7. The method for providing information for selecting an anticancer agent using individual genome sequence variation according to claim 1, wherein the gene sequence variation score is calculated by applying one or more algorithms selected from a group consisting of SIFT (Sorting Intolerant From Tolerant), PolyPhen (Polymorphism Phenotyping), PolyPhen-2, MAPP (Multivariate Analysis of Protein Polymorphism), Logre (Log R Pfam E-value), MutationAssessor, MutationTaster, MutationTaster2, PROVEAN (Protein Variation Effect Analyzer), PMut, Condel, GERP (Genomic Evolutionary Rate Profiling), GERP++, CEO (Combinatorial Entropy Optimization), SNPeffect, fathmm and CADD (Combined Annotation-Dependent Depletion) to gene sequence variation.

8. The method for providing information for selecting an anticancer agent using individual genome sequence variation according to claim 1, wherein the protein damage score or the drug score is calculated by assigning a weighting determined considering a class of the protein, pharmacodynamic or pharmacokinetic classification of the protein, pharmacokinetic parameters of a corresponding drug-metabolizing enzyme, a population group or a race distribution.

9. The method for providing information for selecting an anticancer agent using individual genome sequence variation according to claim 1, wherein the method further comprises determining using the individual drug score whether the anticancer agent will be used for the individual or how it will be used.

10. The method for providing information for selecting an anticancer agent using individual genome sequence variation according to claim 1, wherein the method further comprises receiving the gene sequence variation information involved in the pharmacodynamics or pharmacokinetics of the anticancer agent through a computer system, wherein the computer system comprises or is accessible to a database comprising information about the gene involved in the pharmacodynamics or pharmacokinetics of the anticancer agent.

11. The method for providing information for selecting an anticancer agent using individual genome sequence variation according to claim 1, wherein the method is performed to prevent side effects of the anticancer agent.

12. A system for selecting an anticancer agent using individual genome sequence variation, the system comprising:
a database from which information relevant to a gene or protein related to an anticancer agent applicable to an individual can be searched or extracted;
a communication unit which is accessible to the database;
a non-transitory computer-readable medium storing computer instructions executable by computer, the computer instructions comprising:
(i) a first computer instruction configured to calculate gene sequence variation information of one or more genes involved in pharmacodynamics or pharmacokinetics of the anticancer agent based on the information;
(ii) a second computer instruction configured to calculate a gene sequence variation score using the gene sequence variation information, the gene sequence variation score being a numerical score indicating a degree of variation in the gene that causes an amino acid sequence variation in a protein encoded by the gene or causes a transcription control variation, thereby causing change or damage to a structure or function of the protein;
(iii) a third computer instruction configured to calculate an individual protein damage score using [Equation 2], wherein [Equation 2] is $$S_g(v_1, \ldots, v_n) = \left(\prod_{i=1}^{n} v_i^{w_i}\right)^{\frac{1}{\sum_{i=1}^{n} w_i}}$$

wherein $S_g$ is a protein damage score of a protein encoded by a gene g, n is the number of target sequence variations to be analyzed among sequence variations of the gene g, $v_i$ is a gene sequence variation score of an i-th sequence variation and $w_i$ is a weighting assigned to the gene sequence variation score $v_i$ of the i-th sequence variation; and
(iv) a fourth computer instruction configured to calculate an individual drug score by using [Equation 4], wherein [Equation 4] is:

$$S_d(g_1, \ldots, g_n) = \left(\prod_{i=1}^{n} g_i^{w_i}\right)^{\frac{1}{\sum_{i=1}^{n} w_i}}$$

wherein $S_d$ is a drug score of a drug d, n is the number of proteins encoded by one or more genes involved in the pharmacodynamics or pharmacokinetics of the drug d, $g_i$ is a protein damage score of a protein encoded by one or more genes involved in the pharmacodynamics or pharmacokinetics of the drug d and $w_i$ is a weighting assigned to the protein damage score $g_i$ of the protein encoded by one or more genes involved in the pharmacodynamics or pharmacokinetics of the drug d; and
a display unit which is configured to display information regarding the calculated scores for use in drug selection among anticancer agents.

13. The system for selecting an anticancer agent using individual genome sequence variation according to claim 12, wherein the non-transitory computer-readable medium further comprises a fifth computer instruction configured to determine whether the anticancer agent will be used for the individual using the individual drug score calculated by the fourth computer instruction.

14. The system for selecting an anticancer agent using individual genome sequence variation according to claim 12, wherein the system further comprises a user interface which is configured to calculate and provide an individual drug score for the anticancer agent when the anticancer agent is inputted by a user.

15. The system for selecting an anticancer agent using individual genome sequence variation according to claim 12, wherein the display unit is configured to further display the scores calculated, the calculation procedure, or information used as a ground for the calculation.

16. The system for selecting an anticancer agent using individual genome sequence variation according to claim 12, wherein the gene sequence variation information, the protein damage score, the drug score, and information used as a ground for the calculation are stored in the non-transitory computer-readable medium and the information of stored in the non-transitory computer-readable medium is updated when the database is updated.

17. A non-transitory computer-readable medium including computer instructions for execution by a processor to perform an operation comprising:
    acquiring gene sequence variation information of one or more genes involved in pharmacodynamics or pharmacokinetics of an anticancer agent from individual genome sequence information;
    calculating a gene sequence variation score using the gene sequence variation information, the gene sequence variation score being a numerical score indicating a degree of variation in one of the one or more genes that causes an amino acid sequence variation in a protein encoded by the gene or causes a transcription control variation, thereby causing change or damage to a structure or function of the protein;
    calculating an individual protein damage score using [Equation 2], wherein [Equation 2] is $$S_g(v_1, \ldots, v_n) = \left( \prod_{i=1}^{n} v_i^{w_i} \right)^{\frac{1}{\sum_{i=1}^{n} w_i}}$$

wherein $S_g$ is a protein damage score of a protein encoded by a gene g, n is the number of target sequence variations to be analyzed among sequence variations of the gene g, $v_i$ is a gene sequence variation score of an i-th sequence variation and $w_i$ is a weighting assigned to the gene sequence variation score $v_i$ of the i-th sequence variation; and calculating an individual drug score using [Equation 4], wherein [Equation 4] is:

$$S_d(g_1, \ldots, g_n) = \left( \prod_{i=1}^{n} g_i^{w_i} \right)^{\frac{1}{\sum_{i=1}^{n} w_i}}$$

wherein $S_d$ is a drug score of a drug d, n is the number of proteins encoded by one or more genes involved in the pharmacodynamics or pharmacokinetics of the drug d, $g_i$ is a protein damage score of a protein encoded by one or more genes involved in the pharmacodynamics or pharmacokinetics of the drug d and $w_i$ is a weighting assigned to the protein damage score $g_i$ of the protein encoded by one or more genes involved in the pharmacodynamics or pharmacokinetics of the drug d; and providing the individual drug score for use in drug selection among anticancer agents.

18. The non-transitory computer-readable medium according to claim 17, wherein the operation of the processor further comprises determining using the individual drug score whether the anticancer agent will be used for the individual.

* * * * *

UNITED STATES PATENT AND TRADEMARK OFFICE
CERTIFICATE OF CORRECTION

| | | |
|---|---|---|
| PATENT NO. | : 11,195,594 B2 | Page 1 of 1 |
| APPLICATION NO. | : 15/550004 | |
| DATED | : December 7, 2021 | |
| INVENTOR(S) | : Kim | |

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 1147 days.

Signed and Sealed this
Tenth Day of January, 2023

Katherine Kelly Vidal
*Director of the United States Patent and Trademark Office*